US010767234B2

(12) United States Patent
Abbas et al.

(10) Patent No.: US 10,767,234 B2
(45) Date of Patent: Sep. 8, 2020

(54) METHODS FOR MICROBIAL SCREENING AND IDENTIFICATION OF TARGETS OF INTEREST

(71) Applicant: REGENTS OF THE UNIVERSITY OF MINNESOTA, Minneapolis, MN (US)

(72) Inventors: Abdennour Abbas, Lauderdale, MN (US); Minh-Phuong Ngoc Bui, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/943,000

(22) Filed: Apr. 2, 2018

(65) Prior Publication Data

US 2018/0363032 A1    Dec. 20, 2018

Related U.S. Application Data

(60) Provisional application No. 62/480,242, filed on Mar. 31, 2017.

(51) Int. Cl.
| | | |
|---|---|---|
| *G01N 33/53* | (2006.01) | |
| *C12Q 1/689* | (2018.01) | |
| *C12Q 1/6816* | (2018.01) | |

(52) U.S. Cl.
CPC ........... *C12Q 1/689* (2013.01); *C12Q 1/6816* (2013.01); *G01N 33/53* (2013.01)

(58) Field of Classification Search
CPC ............ C12Q 1/6816; C12Q 2563/137; C12Q 2565/625; C12Q 1/689; G01N 2469/00; G01N 33/52; G01N 33/5308; G01N 33/54306; G01N 33/586; G01N 33/587
See application file for complete search history.

(56) References Cited

FOREIGN PATENT DOCUMENTS

| CN | 101504416 A | 8/2009 |
| EP | 2213311 B1 | 4/2015 |

OTHER PUBLICATIONS

Wang et al ; Food Control (2016), 62, 81-88 (Year: 2016).*
Abbas, "Multifunctional analytical platform on a paper strip: separation, preconcentration, and subattomolar detection" 2013 *Anal. Chem.*, 85:3977-3983.
Abbas, "Trapping proteins within gold nanoparticle assemblies: dynamically tunable hot-spots for nanobiosensing" 2013 *Plasmonics* 8:537-544.
Abbas, "Molecular linker-mediated self-assembly of gold nanoparticles: understanding and controlling the dynamics" 2012 *Langmuir* 29:56-64.
Abbas, "Hot spot-localized artificial antibodies for label-free plasmonic biosensing" 2013 *Adv. Funct. Mater.*, 23:1789-1797.
Armbruster, "Limit of blank, limit of detection and limit of quantitation" 2008 *Clin. Biochem. Rev.* 29:S49-S52.
Aslan, "Metal-enhanced chemiluminescence: advanced chemiluminescence concepts for the 21st century" 2009 *Chemical Society Reviews* 38(9):2556-2564.
ATCC 11842 *Lactobacillus delbrueckii* subsp. *bulgaricus*. (*ATCC 11842*).
ATCC 25922 *Escherichia coli* Castellani and Chalmers.
ATCC MYA3787 *Mucor circinelloides* foodborne pathogen.
Braun, "Surface-enhanced Raman spectroscopy for DNA detection by nanoparticle assembly onto smooth metal films" 2007 *J. Am. Chem. Soc.*, 129:6378-6379.
Bui, "Single-digit pathogen and attomolar detection with the naked eye using liposome-amplified plasmonic immunoassay" 2015 *Nano Lett.*, 15:6239-6246.
Bui, "Gold Nanoplate-Enhanced Chemiluminescence and Macromolecular Shielding for Rapid Microbial Diagnostics" Jul. 2018 *Adv Healthc Mater.*, 7(13):e1701506.
Bui, "Synthesis and Catalytic Properties of Gold Nanoplates and Their Application for Chemiluminscent Detection of Foodborne Microorganisms" 2016 MRS Fall Meeting and Exhibit, Boston MA, Nov. 27, 2016.
Cao, "Gold nanoparticle-based colorimetric assay for selenium detection via hydride generation" 2017 *Anal. Chem.* 89:4695-4700.
Cao, "Nanoparticles with Raman spectroscopic fingerprints for DNA and RNA detection" 2002 *Science* 297:1536-1540.
Chen, "Aggregation-Induced Structure Transition of Protein-Stabilized Zinc/Copper Nanoclusters for Amplified Chemiluminescence" 2015 *ACS Nano*, 9(2): 2173-2183.
Chen, "Tris-(2-carboxyethyl) phosphine significantly promotes the reaction of cisplatin with Sp1 zinc finger protein" 2013 *Chemical Communications*, 49(12): 1226-1228.
Chen, "Peptide functionalized gold nanoparticles for colorimetric detection of matrilysin (MMP-7) activity" 2013 *Nanoscale*,5:8973-8976.
Comotti, "The Catalytic Activity of 'Naked' Gold Particles" 2004 *Angewandte Chemie International Edition*, 43(43):5812-5815.
Daniel, "Gold nanoparticles: assembly, supramolecular chemistry, quantum-size-related properties, and applications toward biology, catalysis, and nanotechnology" 2004 *Chem. Rev.*, 104:293-346.
De Boer, "Methodology for detection and typing of foodborne microorganisms" 1999 *Int J Food Microbiol.*, 50:119-130.
Duan, "Size-Dependent Inhibition and Enhancement by Gold Nanoparticles of Luminol-Ferricyanide Chemiluminescence" 2007 *The Journal of Physical Chemistry C*, 111:4561-4566.

(Continued)

*Primary Examiner* — Padmavathi Baskar
(74) *Attorney, Agent, or Firm* — Meuting Raasch Group

(57) ABSTRACT

Methods of detecting the presence of microorganisms in a sample, the methods including combining a sample, a reducing agent, an oxidant generator and a chemiluminescent agent, and in some cases a shielding agent, wherein the reducing agent both reduces the oxidant generator to produce an oxidant and reduces one or more disulfide bonds on a surface of a microorganism and wherein the oxidant oxidizes the chemiluminescent agent to produce a luminescent compound; and detecting the presence or absence of a signal to indicate the presence or absence of microorganisms in the sample, wherein the intensity of the chemiluminescent signal is inversely proportional to the amount of microorganisms in the sample.

14 Claims, 18 Drawing Sheets

Specification includes a Sequence Listing.

(56) References Cited

OTHER PUBLICATIONS

Dubertret, "Single-mismatch detection using gold-quenched fluorescent oligonucleotides" 2001 *Nature Biotechnol.*, 19:365-70.
Fulford, "Total viable counts, ATP, and endotoxin levels as potential markers of microbial contamination of dental unit water systems" 2004 *Br Dent J*, 196(3): 157-159.
Grabar, "Preparation and characterization of Au colloid monolayers" 1995 *Anal. Chem.*, 67:735-743.
Grisel, "Catalysis by gold nanoparticles" 2002 *Gold Bull.*, 35:39-45.
Haes, "Nanoscale optical biosensor: short range distance dependence of the localized surface plasmon resonance of noble metal nanoparticles" 2004 *J. Phys. Chem. B*, 108:6961-6968.
He, "Colloidal Au-enhanced surface plasmon resonance for ultrasensitive detection of DNA hybridization" 2000 *J. Am. Chem. Soc.*, 122:9071-9077.
Hu, "Plasmonic nanobiosensor based on hairpin DNA for detection of trace oligonucleotides biomarker in cancers" 2015 *ACS Appl. Mater. Interfaces*, 7:2459-2466.
Iranifam, "Enhanced luminol-O2 chemiluminescence reaction by CuO nanoparticles as oxidase mimics and its application for determination of ceftazidime" 2016 *Analytical Methods*, 8(18): 3816-3823.
Juzwik, "Challenges and successes in managing oak wilt in the United States" 2011 *Plant Disease* 95:888-900.
Khan, "Luminol-Based Chemiluminescent Signals: Clinical and Non-clinical Application and Future Uses" 2014 *Appl Biochem Biotechnol.*, 173(2): 333-355.
Kong, "Sensitive and selective colorimetric visualization of cerebral dopamine based on double molecular recognition" 2011 *Angew. Chem., Int Ed.* 50, 1837-1840.
Krężel, "Coordination Properties of Tris(2-carboxyethyl)phosphine, a Newly Introduced Thiol Reductant, and Its Oxide" 2003 *Inorganic Chemistry*, 42(6): 1994-2003.
Lee, "In vivo imaging of hydrogen peroxide with chemiluminescent nanoparticles" 2007 *Nat Mater.*, 6:765-769.
Li, "Chemiluminescent detection of DNA hybridization using gold nanoparticles as labels" 2007 *Anal Bioanal Chem.*, 387:613-618.
Li, "Aminothiols Sensing Based on Fluorosurfactant-Mediated Triangular Gold Nanoparticle-Catalyzed Luminol Chemiluminescence" 2011 *The Journal of Physical Chemistry C*, 115(22): 10964-10970.
Lin, "Gold nanoparticle probes for the detection of mercury, lead and copper ions" 2011 *Analyst* 136:863-871.
Liu, "Silver Nanoparticle-Based Ultrasensitive Chemiluminescent Detection of DNA Hybridization and Single-Nucleotide Polymorphisms" 2006 *Analytical Chemistry*, 78(11):3738-3744.
Liu, "Enzyme-free colorimetric detection of DNA by using gold nanoparticles and hybridization chain reaction amplification" 2013 *Anal. Chem.*, 85:7689-7695.
Lu, "Multifunctional oval-shaped gold-nanoparticle-based selective detection of breast cancer cells using simple colorimetric and highly sensitive two-photon scattering assay" 2010 ACS *Nano* 4:1739-1749.
Luo, "Chemiluminescence biosensors for DNA detection using graphene oxide and a horseradish peroxidase-mimicking DNAzyme" 2012 *Chem. Comm.*, 48:1126-1128.
Magliulo, "A Rapid Multiplexed Chemiluminescent Immunoassay for the Detection of *Escherichia coli* O157:H7, Yersinia enterocolitica, *Salmonella typhimurium*, and Listeria monocytogenes Pathogen Bacteria" 2007 *Journal of Agricultural and Food Chemistry*, 55:4933-4939.
Malhotra, "Nanomaterial-Based Biosensors for Food Toxin Detection" 2014 *Appl Biochem Biotechnol.*, 174:880-896.
Mayer, "Localized surface plasmon resonance sensors" Jun. 2011 *Chem. Rev.*, 111:3828-3857.
Medley, "Gold nanoparticle-based colorimetric assay for the direct detection of cancerous cells" 2008 *Anal. Chem.*, 80:1067-1072.
Millstone, "Colloidal Gold and Silver Triangular Nanoprisms" 2009 *Small*, 5(6): 646-664.

Miranda "One-pot synthesis of triangular gold nanoplates allowing broad and fine tuning of edge length" 2010 *Nanoscale*, 2(10): 2209-2216.
Mostafa, "Shape-Dependent Catalytic Properties of Pt Nanoparticles" 2010 *Journal of the American Chemical Society*, 132(44): 15714-15719.
Narayanan, "Shape-Dependent Catalytic Activity of Platinum Nanoparticles in Colloidal Solution" 2004 *Nano Letters*, 4(7): 1343-1348.
Nelayah, "Mapping surface plasmons on a single metallic nanoparticle" 2007 *Nat. Phys.* 3:348-353.
Nourisaeid, "Colorimetric DNA detection of transgenic plants using gold nanoparticles functionalized with L-shaped DNA probes" 2016 *Physica E*, 75:188-195.
Omidbakhsh, "How Reliable Are ATP Bioluminescence Meters in Assessing Decontamination of Environmental Surfaces in Healthcare Settings?" 2014 *PLoS ONE*, 9(6): e99951.
Overbury, "Comparison of Au catalysts supported on mesoporous titania and silica: investigation of Au particle size effects and metal-support interactions" 2004 *Catal. Lett.*, 95:99-106.
Palchetti, "Electroanalytical biosensors and their potential for food pathogen and toxin detection" May 2008 *Anal Bioanal Chem.*, 391(2):455-71.
Park, "Array-based electrical detection of DNA with nanoparticle probes" 2002 *Science* 295:1503-1506.
Pashazadeh, "Nano-materials for use in sensing of *Salmonella* infections: Recent advances" 2017 *Biosensors and Bioelectronics*, 87:1050-1064.
Pavlov, "Amplified chemiluminescence surface detection of DNA and telomerase activity using catalytic nucleic acid labels" 2004 *Anal. Chem.*, 76:2152-2156.
Pu, "Optical detection of meat spoilage using fluorescence spectroscopy with selective excitation wavelength" 2013 *Appl. Spectrosc.*, 67:210-213.
Qi, "Enhanced effect of aggregated gold nanoparticles on luminol chemiluminescence system and its analytical application" 2013 *Spectrochim. Acta A*, 111:1-6.
Rao, "Size-Dependent Chemistry: Properties of Nanocrystals" 2002 *Chemistry—A European Journal*, 8(1): 28-35.
Ray, "Fungal disease detection in plants: traditional assays, novel diagnostic techniques and biosensors" 2017 *Biosens. Bioelectron.*, 87:708-723.
Roda, "Analytical chemiluminescence and bioluminescence: latest achievements and new horizons" 2012 *Anal. Bioanal. Chem.*, 402:69-76.
Roda, "Progress in chemical luminescence-based biosensors: A critical review" 2016 *Biosensors and Bioelectronics*, 76:164-179.
Rosi, "Nanostructures in biodiagnostics" 2005 *Chem. Rev.*, 105:1547-1562.
Sanchez-Pescador, "Rapid chemiluminescent nucleic acid assays for detection of TEM-1 beta-lactamase-mediated penicillin resistance in Neisseria gonorrhoeae and other bacteria" 1988 *Journal of Clinical Microbiology*, 26:1934-1938.
Scallen, "Foodborne Illness Acquired in the United State—Major Pathogens" 2011 *CDC Emerging Infectious Disease Jour .*, 17(1):19 pgs.
Scheeler, "Plasmon cupling in self-assembled gold nanoparticle-based honeycomb islands" 2013 *J. Phys. Chem. C*, 117:18634-18641.
Sendroiu, "Nanoparticle diffraction gratings for DNA detection on photopatterned glass substrates" 2008 *Biointerphases* 3:FD23-FD29.
Shapaval, "Characterization of food spoilage fungi by FTIR spectroscopy" 2013 *Journal of Applied Microbiology*, 114:788-796.
Singh, "Rapid and PCR-free DNA Detection by Nanoaggregation-Enhanced Chemiluminescence" Oct. 2017 *Scientific Reports*, 7:14011. 9 pgs.
Smith, "Trends in US home food preparation and consumption: analysis of national nutrition surveys and time use studies from 1965-1966 to 2007-2008" 2013 *Nutrition Journal*, 12:45.
Stoeva, "Multiplexed DNA detection with biobarcoded nanoparticle probes" 2006 *Angew. Chem., Int. Ed.*, 45:3303-3306.

(56) References Cited

OTHER PUBLICATIONS

Tangeysh, "Triangular Gold Nanoplate Growth by Oriented Attachment of Au Seeds Generated by Strong Field Laser Reduction" 2015 *Nano Letters*, 15(5): 3377-3382.
Turner, "Selective oxidation with dioxygen by gold nanoparticle catalysts derived from 55-atom clusters" 2008 *Nature*, 454(7207): 981-983.
Valentini, "Gold nanoparticles for naked-eye DNA detection: smart designs for sensitive assays" 2013 *RSC Advances* 3:19181-19190.
Van Der Vossen, "DNA based typing, identification and detection systems for food spoilage microorganisms: development and implementation" 1996 *Int J Food Microbiol.*, 33:35-49.
Willets, "Localized surface plasmon resonance spectroscopy and sensing" 2007 *Annu. Rev. Phys. Chem.*, 58:267-297.
Wu, "Rapid and accurate detection of Ceratocystis fagacearum from stained wood and soil by nested and real-time PCR" 2011 *Forest Pathol.*, 41:15-21.
Xianyu, "A dispersion-dominated chromogenic strategy for colorimetric sensing of glutathione at the nanomolar level using gold nanoparticles" 2015 *Small* 11:5510-5514.
Xu, "A chemiluminescence resonance energy transfer system composed of cobalt(II), luminol, hydrogen peroxide and CdTe quantum dots for highly sensitive determination of hydroquinone" 2016 *Microchimica Acta*, 183:667-673.
Xu, "Ultrasensitive and selective colorimetric DNA detection by nicking endonuclease assisted nanoparticle amplification" 2009 *Angew. Chem., Int. Ed.* 48:6849-6852.
Yang, "Gold nanoparticle-based exonuclease III signal amplification for highly sensitive colorimetric detection of folate receptor" 2014 *RSC Nanoscale* 6:3055-3058.
Yang, "Use of nested and real-time PCR for the detection of Ceratocystis fagacearum in the sapwood of diseased oak species in Minnesota" 2016 *Plant Disease* 101:480-486.
Yeh, "Enhancement in Chemiluminescence by Carbonate for Cobalt(II)-catalyzed Oxidation of Luminol with Hydrogen Peroxide" 2005 *Journal of the Chinese Chemical Society*, 52(4):657-664.
Yeo, "A Multiplex Two-Color Real-Time PCR Method for Quality-Controlled Molecular Diagnostic Testing of FFPE Samples" 2014 *PLoS ONE*, 9:e89395.
Zeng, "A Comparison Study of the Catalytic Properties of Au-Based Nanocages, Nanoboxes, and Nanoparticles" 2010 *Nano Letters*, 10(1):30-35.
Zhang, "Ultrasensitive Flow Injection Chemiluminescence Detection of DNA Hybridization Using Signal DNA Probe Modified with Au and CuS Nanoparticles" 2008 *Analytical Chemistry*, 80(19):7206-7212.
Zhang, "Chemiluminescence sensing of aminothiols in biological fluids using peroxymonocarbonate-prepared networked gold nanoparticles" 2013 *Analyst*, 138:850-855.
Zhang, "Photocatalytic oxidation of TMB with the double stranded DNA-SYBR Green I complex for label-free and universal colorimetric bioassay" 2015 *Chem. Commun.*, 51:14465-14468.
Zhang, "Gold nanoparticle-catalyzed luminol chemiluminescence and its analytical applications" 2005 *Anal. Chem.*, 77:3324-3329.
Zhao, "A disposable amperometric enzyme immunosensor for rapid detection of Vibrio parahaemolyticus in food based on agarose/Nano-Au membrane and screen-printed electrode" Jun. 2007 *Electrochemistry Communications*, 9(6):1263-1268.
Zhao, "Ultrasensitive DNA detection using highly fluorescent bioconjugated nanoparticles" 2003 *J. Am. Chem. Soc.*, 125:11474-11475.
Zhou, "Size-Dependent Catalytic Activity and Dynamics of Gold Nanoparticles at the Single-Molecule Level" 2010 *Journal of the American Chemical Society*, 132(1): 138-146.

\* cited by examiner

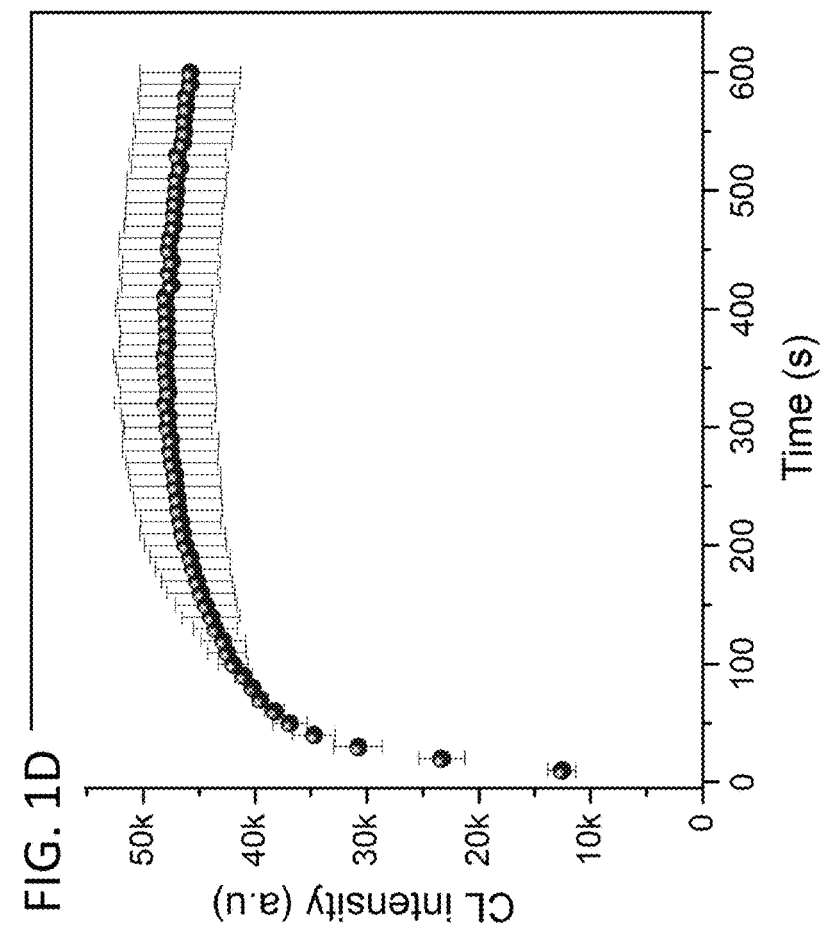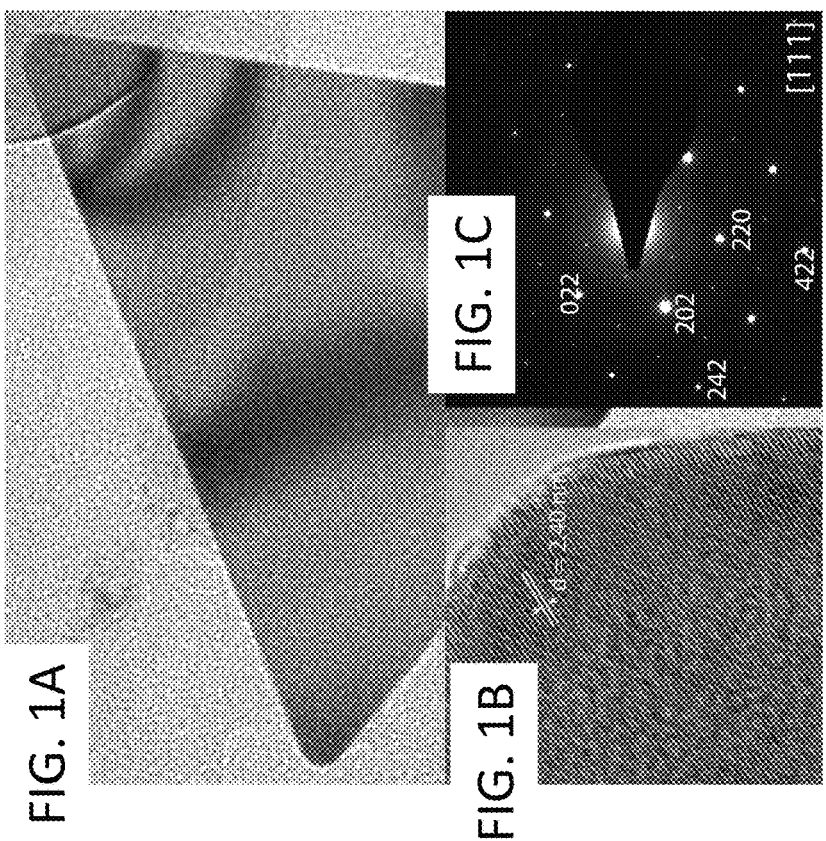
FIG. 1A FIG. 1B FIG. 1C FIG. 1D

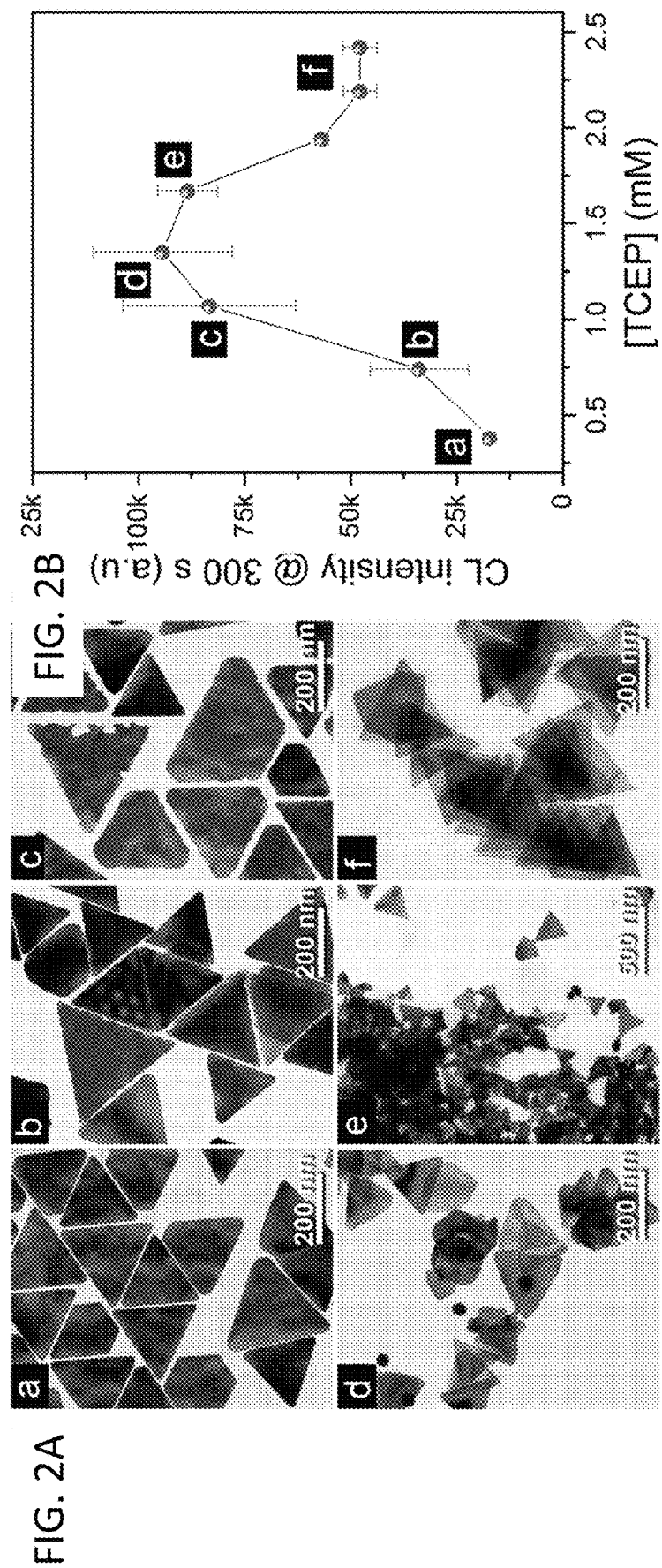

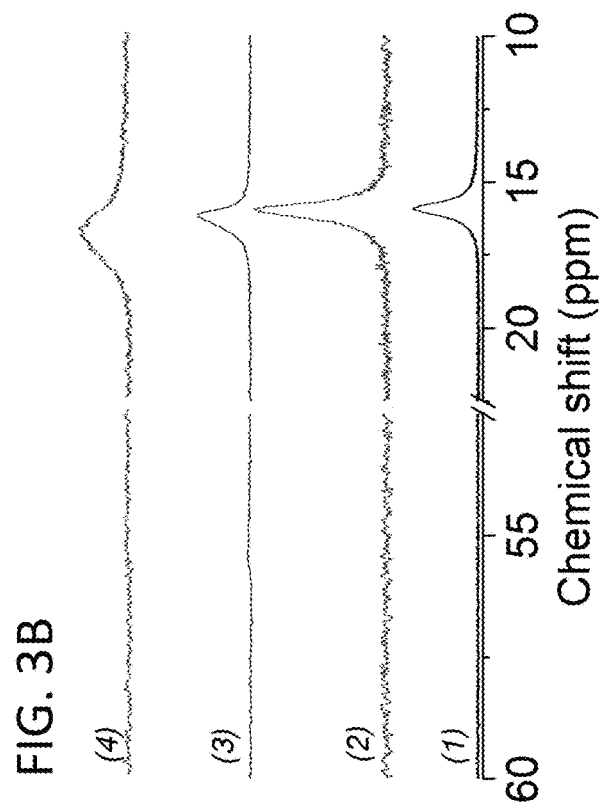
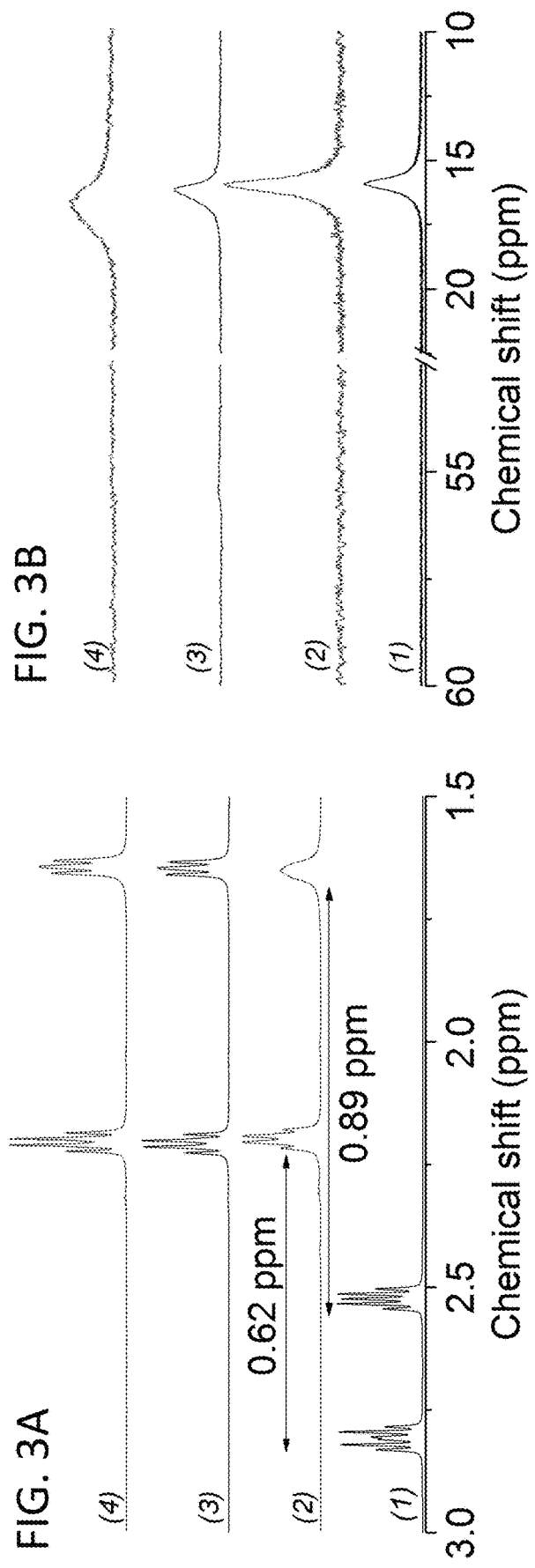
FIG. 3B
FIG. 3A

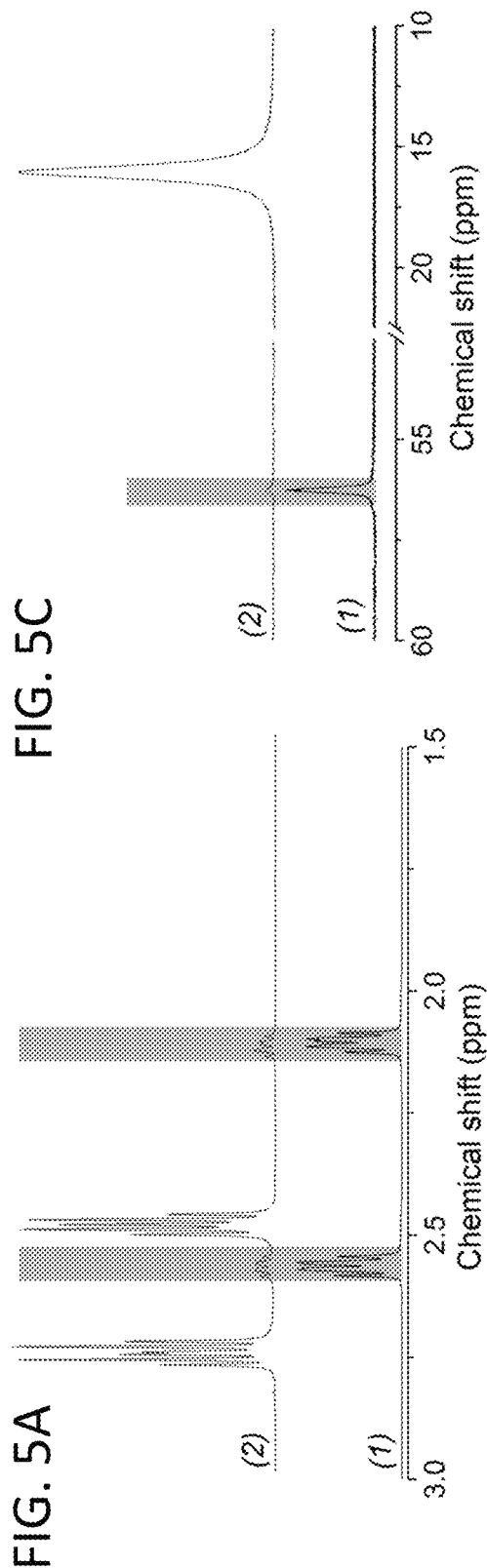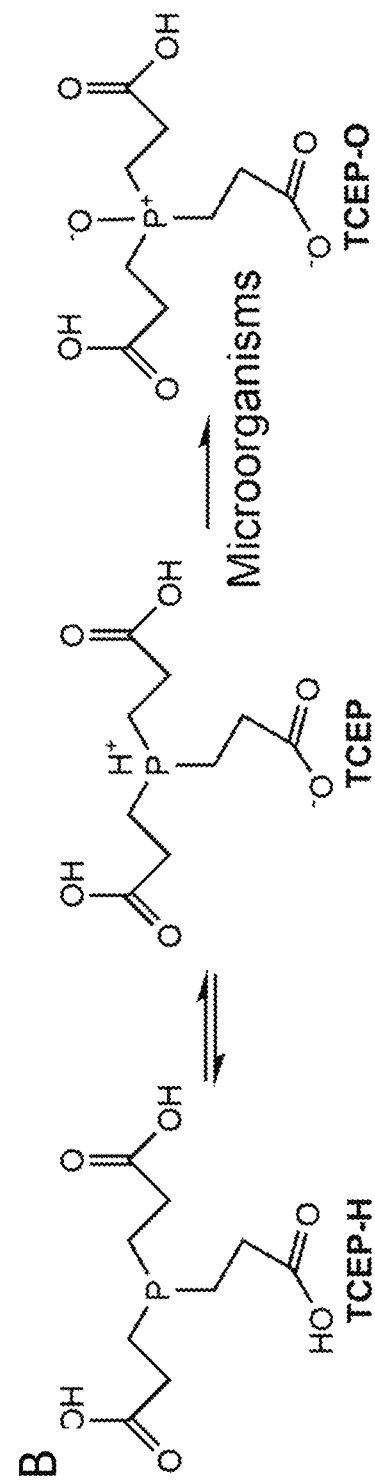

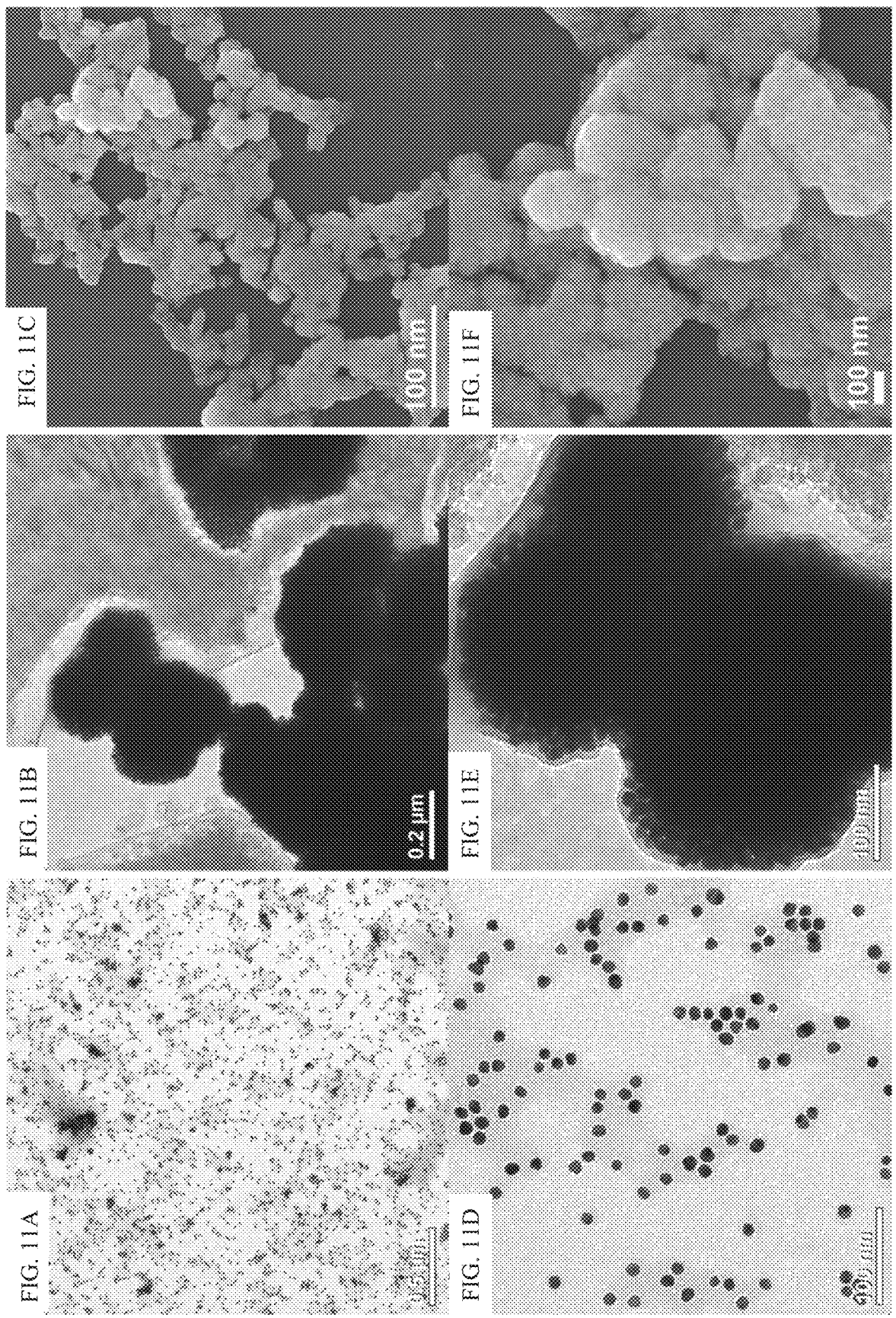

METHODS FOR MICROBIAL SCREENING AND IDENTIFICATION OF TARGETS OF INTEREST

CROSS-REFERENCE TO RELATED APPLICATIONS

This application claims the benefit of U.S. Provisional Application Ser. No. 62/480,242, filed Mar. 31, 2017, which is incorporated by reference herein.

SEQUENCE LISTING

This application contains a Sequence Listing electronically submitted via EFS-Web to the United States Patent and Trademark Office as an ASCII text file entitled "11005640101_ST25.txt" having a size of 4 kilobytes and created on Aug. 6, 2018. The information contained in the Sequence Listing is incorporated by reference herein.

GOVERNMENT FUNDING

This invention was made with government support under contract number 1605191 awarded by the National Science Foundation. The government has certain rights in this invention.

BACKGROUND

Rapid detection of microorganisms in food processing industry and clinical hospitals is becoming more important. Foodborne diseases affect as many as 81 million persons in the United States each year with an estimated annual cost of $8-10 billion (E, S.; R M, H.; F J, A.; R V, T.; M-A, W.; S L, R. 2011). Moreover, changes in lifestyle in the 21st century (e.g. more meals eaten outside the home) have increased the opportunities for transmission of pathogenic bacteria through foods (Smith, L. P.; Ng, S. W.; Popkin, B. M. Nutrition Journal 2013, 12, 45-45). Therefore, rapid methods for detecting microorganism and pathogenic bacteria can help prevent foodborne disease through better control of processed foods. The methods would have the ability to rapidly screen for quality control at a processing facility, which will reduce costs and expedite distribution of products. Conventional methods require isolation and identification after labor and time intensive enrichment and plating procedures which take more than 24 h.

Furthermore, target hybridization with a labeled nucleotide probe has become one of the most widely used methods for detection of sequence-specific DNA. Chemiluminescence, light emission by a chemical reaction, is an attractive analytical tool for detection and quantification of a wide variety of applications. Applications of chemiluminescence for nucleic acid detection have routinely used enzymes such as peroxidase to generate or enhance the chemiluminescence of luminol, however the use of enzymes can make such methods less desirable.

SUMMARY

Disclosed herein are methods of detecting the presence of microorganisms in a sample, the methods including combining a sample, a reducing agent, an oxidant generator and a chemiluminescent agent, wherein the reducing agent both reduces the oxidant generator to produce an oxidant and reduces one or more disulfide bonds on a surface of a microorganism and wherein the oxidant oxidizes the chemiluminescent agent to produce a luminescent compound; and detecting the presence or absence of a signal to indicate the presence or absence of microorganisms in the sample, wherein the intensity of the chemiluminescent signal is inversely proportional to the amount of microorganisms in the sample.

Also disclosed herein are methods method of detecting the presence of a specific class or type of microorganism in a sample, the methods including combining a first aliquot of a sample, a reducing agent, an oxidant generator and a chemiluminescent agent, wherein the reducing agent both reduces the oxidant generator to produce an oxidant and reduces one or more disulfide bonds on a surface of a microorganism and wherein the oxidant oxidizes the chemiluminescent agent to produce a luminescent compound; detecting the presence or absence of a first signal from the luminescent compound to indicate the presence or absence of total microorganisms in the first aliquot of the sample, wherein the intensity of the signal is inversely proportional to the amount of total microorganisms in the sample; combining a second aliquot of the sample with a shielding agent, the shielding agent including a receptor; and a macromolecular polymer, wherein the shielding agent binds via the receptor only to the specific class or specific type of microorganism and not to other classes or other types respectively of microorganisms in the sample; combining the second aliquot of the sample and the shielding agent with a reducing agent, an oxidant generator and a chemiluminescent agent, wherein the reducing agent both reduces the oxidant generator to produce an oxidant and reduces one or more disulfide bonds on surfaces of microorganisms not bound to the shielding agent and wherein the oxidant oxidizes the chemiluminescent agent to produce a luminescent compound; and detecting the presence or absence of a second signal.

Also disclosed are methods of detecting the presence of a target of interest in a sample where the method includes combining a sample, a plasmonic material-probe complex, an oxidant and a chemiluminescent agent, wherein the plasmonic material-probe complex includes a probe having a length that allows plasmonic material-probe complexes to form dimers when the target of interest hybridizes thereto and wherein the oxidant oxidizes the chemiluminescent agent to produce a luminescent compound; and detecting the presence of the target of interest in the sample based on increased intensity of the luminescent signal as compared to a sample without the target of interest.

The above summary of the disclosure is not intended to describe each disclosed embodiment or every implementation of the disclosure. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

BRIEF DESCRIPTION OF FIGURES

FIGS. 1A to 1D show TEM images of synthetic AuNT particle, size: 200 nm (FIG. 1A); its HR-TEM image (FIG. 1B); its corresponding electron diffraction pattern (FIG. 1C); and the chemiluminescence prolife of luminol and TCEP in the presence of AuNT (FIG. 1D).

FIGS. 2A and 2B are TEM images of Au nanoplates oxidized by chemical reaction with different concentration of TCEP in the presence of luminol (FIG. 2A)—the concentration of TCEP (mM) were (a): 0.38; (b): 0.74; (c): 1.07; (d): 1.35; (e): 1.67; (g): 1.94; (Gg): 2.42 mM); and the correlation plot FIG. 2B.

FIGS. 3A and 3B are $^1$H (FIG. 3A) and $^{31}$P NMR (FIG. 3B) spectra of TCEP (a) and its interaction with Luminol (b), with Au nanoplates (c), with Au nanoplates+Luminol (d).

FIGS. 5A and 5C show $^1$H (FIG. 5A) and $^{31}$P (FIG. 5C) NMR spectra of oxidized TCEP form (TCEP-O) (curve a) and its composition after interact with E. coli solution ($10^7$ cfu/mL) (curve b). Two new $^1$H NMR peaks and a new $^{31}$P NMR peak at 56 ppm corresponding to TCEP-O form were observed. FIG. 5B illustrates the interaction of TCEP with E. coli resulting in the reduction of the disulfide bond on the microbial surface. Schematic of TCEP attach on disulfide bridge to generate free thiol group and oxidation form of TCEP (TCEP-O).

FIGS. 11A, 11B, 11C, 11D, 11E and 11F show electron microscopy images of AuNPs conjugated with DNA probes before and after aggregation with target DNA-TEM image of AuNPs-DNA probes (no target DNA added) (FIG. 11A); TEM image of AuNPs-DNA probes in the presence of the target DNA (FIG. 11B); SEM image of AuNPs-DNA probes in the presence of the target DNA (FIG. 11C). FIGS. 11D, 11E and 11F are zoomed views of FIGS. 11D, 11E and 11F respectively.

DETAILED DESCRIPTION OF ILLUSTRATIVE EMBODIMENTS

Figure 1E:
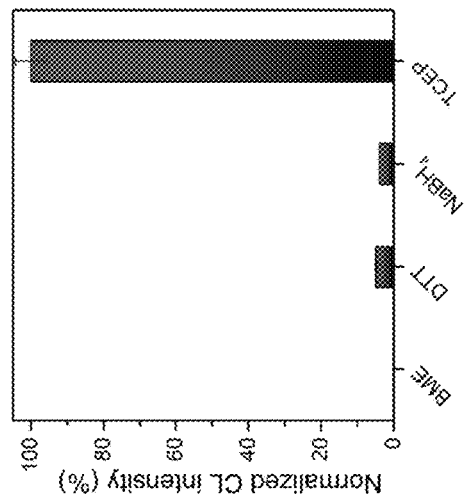
FIGS. 1E to 1I show the UV-visible spectrum of the synthesized Au nanoplates (FIG. 1E); the effect on chemiluminescence (%) of various reducing agents in the presence of Au nanoplates (FIG. 1F); the effect of mixing luminol with various reducing agents on chemiluminescence (FIG. 1G); the effect on chemiluminescence of replacing Au nanoplates with gold nanoparticles or gold nanorods (FIG. 1H); and a TEM image of AuNT (FIG. 1I).

Chemiluminescence, light emission induced by chemical reaction, has been an attractive technique in analytical chemistry with a variety of applications in food science and medicine due to its simplicity, high sensitivity, low background noise and wide linear dynamic range (Roda, A.; Mirasoli, M.; Michelini, E.; Di Fusco, M.; Zangheri, M.; Cevenini, L.; Roda, B.; Simoni, P. Biosensors and Bioelectronics 2016, 76, 164-179; Magliulo, M.; Simoni, P.; Guardigli, M.; Michelini, E.; Luciani, M.; Lelli, R.; Roda, A. Journal of Agricultural and Food Chemistry 2007, 55, 4933-4939; and Roda, A.; Guardigli, M. Analytical and Bioanalytical Chemistry 2012, 402, 69-76). There are many different chemical reactions used to generate chemiluminescence signals including potassium ferricyanide ($K_3[Fe(CN)_6]$), luminol, diphenyl oxalate with hydrogen peroxide ($H_2O_2$) in the presence of a metal ion ($Fe^{3+}$, $Cu^{2+}$, $K^+$) catalyst (Xu, S.; Li, J.; Li, X.; Su, M.; Shi, Z.; Zeng, Y.; Ni, S. Microchimica Acta 2016, 183, 667-673; Duan, C.; Cui, H.; Zhang, Z.; Liu, B.; Guo, J.; Wang, W. The Journal of Physical Chemistry C 2007, 111, 4561-4566; and Zhang, L.; Lu, B.; Lu, C. Analyst 2013, 138, 850-855). The most common luminescence reactions occur in living systems.

Bioluminescence from fireflies, jellyfish and crustacean which uses luciferin and its enzyme, luciferase, to generate bioluminescence signal. However, chemiluminescence signal in those reactions is quickly deceased and only lasts for a few seconds, which is inconvenient for analytical applications.

Many commercially available detection technologies are labeled for "rapid microbial detection", however, they often require 12-48 hours enrichment before detection including the BAX® system and lateral flow assays offered by Dupont Inc., ATP Bioluminescence and Petrifilm plates from 3M, Pathatrix system from Fisher Scientific and BacT/ALERT system from Biomerieux. Because of the required time frame and large scale voume of sample, the food industry prefers to rely on much cheaper cell culture and microscopic identification techniques. In chemiluminescence systems, a number of chemicals pair together to generate signals including luminol-$H_2O_2$, luminol-$K_3Fe(CN)_6$, $NaHCO_3$—$H_2O_2$ and luciferin-luciferase etc. In these systems, nanoparticles such as Au, Ag, Pt, Zn/Cu also participate in CL reaction as reductants, catalysts, and luminophores by decomposing $H_2O_2$ to produce reactive oxygen species and enhance the CL signal (Zhang, S.; Zhong, H.; Ding, C. *Analytical Chemistry* 2008, 80, 7206-7212; Lee, D.; Khaja, S.; Velasquez-Castano, J. C.; Dasari, M.; Sun, C.; Petros, J.; Taylor, W. R.; Murthy, N. *Nat Mater* 2007, 6, 765-769; Liu, C.-H.; Li, Z.-P.; Du, B.-A.; Duan, X.-R.; Wang, Y.-C. *Analytical Chemistry* 2006, 78, 3738-3744; and Pashazadeh, P.; Mokhtarzadeh, A.; Hasanzadeh, M.; Hejazi, M.; Hashemi, M.; de la Guardia, M. *Biosensors and Bioelectronics* 2017, 87, 1050-1064). However, the light emission from chemical reaction of luminol with $H_2O_2$ and other quickly fades (usually within 1 second) which limits its practical application. A number of commercial ATP-bioluminescent kits and equipment are commercially available. However, their application is limited due to the need of cell enrichment to reach a detectable signal (Zhang, S.; Zhong, H.; Ding, C. *Analytical Chemistry* 2008, 80, 7206-7212; Lee, D.; Khaja, S.; Velasquez-Castano, J. C.; Dasari, M.; Sun, C.; Petros, J.; Taylor, W. R.; Murthy, N. *Nat Mater* 2007, 6, 765-769; Liu, C.-H.; Li, Z.-P.; Du, B.-A.; Duan, X.-R.; Wang, Y.-C. *Analytical Chemistry* 2006, 78, 3738-3744; Pashazadeh, P.; Mokhtarzadeh, A.; Hasanzadeh, M.; Hejazi, M.; Hashemi, M.; de la Guardia, M. *Biosensors and Bioelectronics* 2017, 87, 1050-1064; and Chen, H.; Lin, L.; Li, H.; Li, J.; Lin, J.-M. *ACS Nano* 2015, 9, 2173-2183).

Given the limitations of previously utilized techniques, rapid testing of microbial content in food and environmental samples has become more important. Spoilage of food by bacteria and fungi not only presents a quality concern, but also a food safety issue. Mold species can produce mycotoxins in food which directly affects consumer health. The main method for detection of fungi, cell plating, even take longer time (from 5 to 7 days) in comparison to bacteria. Some commercial products such as 3M PETRIFILM®, CHEMUNEX® from bioMérieux (Etoile, France), BioLumix from Neogen Corp. (Lansing, Mich.), BAX® from Dupont (Wilmington, Del.) claims to cut down the incubation time but all require processing time still from 24 to 72 hours. Nucleic acid based assays used for detection of methicillin-resistant *Staphylococcus aureus* (MRSA)bacteria can reduce the time to 4 hours, but sensitivity was still at the $10^4$ to $10^5$ cfu/mL (Sanchez-Pescador, R.; Stempien, M. S.; Urdea, M. S. *Journal of Clinical Microbiology* 1988, 26, 1934-1938; de Boer, E.; Beumer, R. R. *Int J Food Microbiol* 1999, 50, 119-130; Pu, Y.; Wang, W.; Alfano, R. R. *Appl. Spectrosc.* 2013, 67, 210-213; Shapaval, V.; Schmitt, J.; Møretrø, T.; Suso, H. P.; Skaar, I.; Åsli, A. W.; Lillehaug, D.; Kohler, A. *Journal of Applied Microbiology* 2013, 114, 788-796; Van Der Vossen, J. M. B. M.; Hofstra, H. *Int J Food Microbiol* 1996, 33, 35-49; Yeo, J.; Crawford, E. L.; Blomquist, T. M.; Stanoszek, L. M.; Dannemiller, R. E.; Zyrek, J.; De Las Casas, L. E.; Khuder, S. A.; Willey, J. C. *PLoS ONE* 2014, 9, e89395; and Malhotra, B.; Srivastava, S.; Ali, M. A.; Singh, C. *Appl Biochem Biotechnol* 2014, 174, 880-896).

In some embodiments, disclosed methods can be utilized to detect one or more microorganisms in a composition, solution or sample. In some embodiments, disclosed methods can be utilized to identify one or more microorganisms, the class of a microorganism present, or some combination thereof in a composition, solution or sample. In some embodiments, disclosed methods can be utilized to quantify one or more microorganisms in a composition, solution or sample. In some embodiments, disclosed methods can be utilized to concentrate one or more microorganisms in a composition, solution or sample. In some embodiments, disclosed methods can be utilized to separate one or more microorganisms in a composition, solution or sample. In some embodiments, disclosed methods can be utilized to manipulate one more microorganisms in a composition, solution or sample. In some embodiments, disclosed methods can be utilized to detect, identify, quantify, concentrate, separate, manipulate, affect or any combination thereof one or more microorganisms in a composition, solution or sample.

As used herein "microorganism" will include bacteria (e.g., gram positive bacteria, gram negative bacteria and others), fungi (e.g., yeasts, molds and others), Archaea, protists (e.g. algae), viruses, any microscopic unicellular or multicellular organism or microscopic biological material (e.g., eukaryotic cells, and organelles), or combinations thereof.

Disclosed methods may be useful for "microbial screening", which, as used herein means the detection, quantification, or some combination thereof of total microbial content (e.g., the total amount of microorganisms), detection, quantification or some combination thereof of the presence of fungi, bacteria, or viruses, or any combinations thereof (for example). All microorganisms include protein molecules having disulfide bridges on their surfaces. Disclosed methods competitively react a reducing agent with an oxidant generator and the disulfide bridges on microorganisms that may be present in a sample, thereby providing a quantity of oxidant that is dependent on the quantity of microorganisms in the sample, to oxidize a chemiluminescent agent to a luminescent compound.

Disclosed methods can also be utilized to identify, quantify or both, specific microbial classes, specific microbial types, specific microbial species, or specific microbial strain. Detection, identification, quantification, or combinations thereof of specific microbial classes, specific microbial types, specific microbial species, or specific microbial strains can be accomplished by combining the sample with a shielding agent prior to combining the reducing agent with the sample. Shielding agents as utilized herein include a receptor that is coupled to a macromolecular polymer. As used herein, a "receptor" includes molecules or biomolecules with recognition abilities (e.g., nucleic acids, aptamers, antibodies, enzymes or any other protein or molecule with recognition abilities) for a class of microorganisms or species of microorganisms. The receptor of the shielding agent causes the shielding agent to interact only with a targeted class or species of microorganisms and the macromolecular polymer shields the disulfide bridge proteins on the surface of the microorganism from being reduced by the reducing agent.

Disclosed herein are methods of detecting the presence of one or more microorganisms, referred to generally as microorganisms, in a sample. Such methods can include steps of combining a sample, a reducing agent, an oxidant generator and a chemiluminescent agent together. The reducing agent competitively reduces the oxidant generator to produce an oxidant and one or more disulfide bonds on a surface of a microorganism. As used herein, an "oxidant" can refer to any oxidizing agent including reactive oxygen species including for example peroxides, superoxide, hydroxyl radical, and singlet oxygen. The oxidant in turn oxidizes the chemiluminescent agent to produce a luminescent compound. Then, the presence or absence of a signal from the luminescent compound can be detected in order to indicate the presence or absence of microorganisms in the sample. The intensity (or presence) of the luminescent signal is inversely proportional to the amount of microorganisms in the sample.

More specifically, disclosed herein is a chemical reaction that generates a luminescent signal based on the reaction of a reducing agent with a chemiluminescent agent in the presence of an oxidant generator. Even more specifically, disclosed herein is a chemical reaction that generates a consistent luminescence signal for a long period of time (e.g., up to one hour) based on the reaction of TCEP with luminol in the presence, e.g. on the surface of gold nanoplatelets. The reaction of the reducing agent with both the surface of microorganisms via reduction of disulfide groups and the generation of an oxidant to oxidize the chemiluminescent agent provides the ability to screen total microorganisms in a simple step.

Although detection of total microorganisms using disclosed reactions is quick and simple, disclosed herein is also specific detection of microorganisms or classes of microorganisms, which is perhaps even more important in practical diagnostic tests. In such methods, specific receptors, such as antibodies or aptamers (short polynucleotide sequence) can be used for specific binding to a target of interest. Such a receptor in conjugation to a macromolecular polymer, the combination of which is referred to as a shielding agent can act as a shield for specific microorganisms or classes of microorganisms against interaction with the reducing agent. The shielding agent (receptor-macropolymer polymer) can be added to the sample before the reducing agent is added. In such a configuration, the shielding agent would not allow the microorganisms that bind with the receptor in the shielding agent to be reduced. Such two-step analytical methods can simultaneously provide both screening and specific detection of microorganisms in clinical, food, and environmental samples with high sensitivity and specificity. By comparing a non-shielded then reduced sample with a shielded then reduced sample, the amount of microorganisms which bind to the receptor in the shielding agent can be determined.

Useful reducing agents that can be utilized herein can include, for example tris(2-carboxyethyl)phosphine (TCEP), tris(2-carboxyethyl)phosphine hydrochloride (TCEP-HCl), other compositions including TCEP, any reducing agent containing one or more hydroxyl or carboxyl groups, or combinations thereof. In some embodiments, TCEP or TCEP-HCl can be utilized.

Useful chemiluminescent agents that can be utilized herein can include, for example luminol.

Useful oxidant generators that can be utilized herein can include for example gold, copper, zinc, or combinations thereof. In some embodiments, gold can be utilized. In some embodiments, gold nanoparticles can be utilized. In some embodiments, gold nanoparticles having relatively sharp angles may be useful because they provide an enhanced effect due to the catalytic effect of the sharp angles on chemical reactions. A specific, illustrative example is gold nanoplates or gold nanotriangles having an average size of 200±25 nm and thicknesses not greater than 5 nm.

As discussed above, shielding agents include both a receptor and a macromolecular polymer. A receptor in the shielding agent is designed to bind to a specific type or specific class of microorganisms and not to other types or other classes respectively of microorganisms. Illustrative receptors that can be utilized herein can depend at least in part on the specific class or microorganism or specific microorganism that is of interest, but can include antibodies, enzymes, aptamers, or molecular receptors for example. Illustrative macromolecular polymers that can be utilized herein can include chitosan, polyethylene glycol (PEG), or combinations thereof. In some embodiments, any organic or organometallic polymer that has an overall charge (zeta potential) opposite to the surface charge or zeta potential of the target microorganism can be utilized as the macromolecular polymer. Such materials may provide advantageous results, prevent non-specific shielding, or both.

Also disclosed herein are methods that include using disclosed shielding agents with other types of detection. In such methods, the shielding agent prevents or decreases the ability of the specific class, specific type, specific species or specific strain of microorganism (or molecule or biomolecule) from interacting with a detection agent. A "detection agent" is an agent that directly or indirectly generates a signal upon interaction with the specific class, specific type, specific species or specific strain of microorganism. The absence or decrease in the signal after shielding can indicate the presence of the target analyte (e.g., the specific class, specific type, specific species or specific strain of microorganism, molecule or biomolecule for example). The detection agent could generate any type of signal, examples of which can include optical (luminescence, fluorescence, absorbance, colorimetry, plasmonic), electrical, calorimetric electrochemical, piezoelectric or nuclear magnetic resonance signals or combination thereof.

Also disclosed herein are therapeutic methods that include the use of disclosed shielding agents. Such methods can be utilized to prevent or decrease interaction of a toxin or a pathogen such as bacteria, viruses, fungi, parasites, prions or other microorganisms with a cell, tissue or unicellular or multicellular organism. Disclosed methods can include a step of combining disclosed shielding agents with the cell, tissue or unicellular or multicellular organism to be protected from the interaction. The shielding agent can then bind to the microorganism of interest, thereby hindering or eliminating its ability to interact with or affect the cell, tissue or unicellular or multicellular organism.

Also disclosed herein are methods that include use of a reducing agent on the oxidant generator to catalyze any type of chemical or biochemical reaction that requires an oxidant. Such methods could have applicability in industrial applications in order to activate reactions, enhance the yield of reactions, or combinations thereof.

Some illustrative embodiments disclosed herein include methods of detecting the presence of microorganisms in a sample, the methods including combining a sample, a reducing agent, an oxidant generator and a chemiluminescent agent, wherein the reducing agent both reduces the oxidant generator to produce an oxidant and reduces one or more disulfide bonds on a surface of a microorganism and wherein the oxidant oxidizes the chemiluminescent agent to produce a luminescent compound; and detecting the presence or absence of a signal from the luminescent compound to indicate the presence or absence of microorganisms in the sample, wherein the intensity of the signal is inversely proportional to the amount of microorganisms in the sample.

In some such embodiments, the methods can further include combining the sample with a shielding agent before combining it with the reducing agent. In some such embodiments, the methods can further include subjecting another sample to the combining and detecting steps and comparing the signals between the two samples to determine an amount of a specific type or class of microorganism. In some such embodiments, the reducing agent can include a compound containing one or more hydroxyl or carboxyl groups. In some such embodiments, the reducing agent can include tris(2-carboxyethyl)phosphine (TCEP). In some such embodiments, the chemiluminescent agent can include luminol. In some such embodiments, the oxidant generator can include gold, copper, zinc, or combinations thereof. In some such embodiments, the oxidant generator can include gold nanoparticles. In some such embodiments, the oxidant generator can include gold nanoplates or gold nanotriangles. In some such embodiments, the oxidant generator can include gold nanoplates or gold nanotriangles having an average size of 200+25 nm and thicknesses less than 5 nm. In some such embodiments, the shielding agent can include a receptor and a macromolecular polymer. In some such embodiments, the receptor can include antibodies, enzymes, aptamers, or molecular receptors. In some such embodiments, the macromolecular polymer can include chitosan, polyethylene glycol (PEG), or combinations thereof. In some such embodiments, the macromolecular polymer can include organic polymer, organometallic polymer, or combinations thereof that have an overall charge (zeta potential) opposite to the surface charge or zeta potential of the target microorganism.

Some illustrative embodiments disclosed herein include methods of detecting the presence of a specific class, specific type, specific species or specific strain of microorganism in a sample, the methods including combining a first aliquot of a sample, a reducing agent, an oxidant generator and a chemiluminescent agent, wherein the reducing agent both reduces the oxidant generator to produce an oxidant and reduces one or more disulfide bonds on a surface of a microorganism and wherein the oxidant oxidizes the chemiluminescent agent to produce a luminescent compound; detecting the presence or absence of a first signal from the luminescent compound to indicate the presence or absence of total microorganisms in the first aliquot of the sample, wherein the intensity of the signal is inversely proportional to the amount of total microorganisms in the sample; combining a second aliquot of the sample with a shielding agent, the shielding agent comprising a receptor; and a macromolecular polymer, wherein the shielding agent binds via the receptor only to the specific class, specific type, specific species or specific strain of microorganism and not to other classes or other types, species or strains respectively of microorganisms in the sample; combining the second aliquot of the sample and the shielding agent with a reducing agent, an oxidant generator and a chemiluminescent agent, wherein the reducing agent both reduces the oxidant generator to produce an oxidant and reduces one or more disulfide bonds on surfaces of microorganisms not bound to the shielding agent and wherein the oxidant oxidizes the chemiluminescent agent to produce a luminescent compound; and detecting the presence or absence of a second signal.

In some such embodiments, the methods can further include combining the sample with a shielding agent before combining it with the reducing agent. In some such embodiments, the methods can further include subjecting another sample to the combining and detecting steps and comparing the signals between the two samples to determine an amount of a specific type or class of microorganism. In some such embodiments, the reducing agent can include a compound containing one or more hydroxyl or carboxyl groups. In some such embodiments, the reducing agent can include tris(2-carboxyethyl)phosphine (TCEP). In some such embodiments, the chemiluminescent agent can include luminol. In some such embodiments, the oxidant generator can include gold, copper, zinc, or combinations thereof. In some such embodiments, the oxidant generator can include gold nanoparticles. In some such embodiments, the oxidant generator can include gold nanoplates or gold nanotriangles. In some such embodiments, the oxidant generator can include gold nanoplates or gold nanotriangles having an average size of 200+25 nm and thicknesses less than 5 nm. In some such embodiments, the shielding agent can include a receptor and a macromolecular polymer. In some such embodiments, the receptor can include antibodies, enzymes, aptamers, or molecular receptors. In some such embodiments, the macromolecular polymer can include chitosan, polyethylene glycol (PEG), or combinations thereof. In some such embodiments, the macromolecular polymer can include organic polymer, organometallic polymer, or combinations thereof that have an overall charge (zeta potential) opposite to the surface charge or zeta potential of the target microorganism.

Some illustrative embodiments disclosed herein include methods of preventing or affecting the ability of a specific class, specific type, specific species or specific strain of microorganism to interact with a cell, tissue, or unicellular or multicellular organism, the methods including combining a shielding agent with the cell, tissue, or unicellular or multicellular organism, the shielding agent comprising a receptor; and a macromolecular polymer, wherein the shielding agent binds via the receptor to the specific class, specific type, specific species or specific strain of microorganism, thereby affecting or hindering the ability of the specific class, specific type, specific species or specific strain of microorganism to interact with the cell, tissue, or unicellular or multicellular organism. In some such methods, the method can be carried out for therapeutic purposes.

Some illustrative embodiments disclosed herein include methods of detecting the presence of a specific class, specific type, specific species or specific strain of microorganism in a sample, the methods including combining a sample with a shielding agent, the shielding agent including a receptor; and a macromolecular polymer, wherein the shielding agent binds via the receptor only to the specific class, specific type, specific species or specific strain of microorganism and not to other classes or other types, species or strains respectively of microorganisms in the sample; combining the sample and the shielding agent with a detection agent, wherein the shielding agent prevents or decreases the ability of the specific class, specific type, specific species or specific strain of microorganism from interacting with the detection agent and wherein the detection agent produces a signal; and detecting the presence or absence of the signal.

In some such methods, the signal is optical, electrical, calorimetric electrochemical, piezoelectric, nuclear magnetic resonant, or any combination thereof. In some such methods, the optical signal is luminescence, fluorescence, absorbance, colorimetry, plasmonic.

Some illustrative embodiments disclosed herein include methods of catalyzing a chemical or biochemical reaction, the methods including combining a reducing agent with an oxidant generator in a chemical or biochemical reaction mixture, wherein the reducing agent acts on the oxidant generator to form an oxidant that activates, catalyzes, enhances, or some combination thereof the chemical or biochemical reaction.

Some illustrative methods include combining a sample with a plasmonic material-probe complex, an oxidant, and a chemiluminescent agent. The oxidant and the chemiluminescent agent can include features such as those described above. Specifically, the oxidant is one that can oxidize the chemiluminescent agent to produce a luminescent compound.

Useful plasmonic materials that can be utilized herein can include for example gold, copper, aluminum, or combinations thereof. In some embodiments, gold can be utilized. In some embodiments, gold nanoparticles can be utilized. Specific, illustrative examples include gold nanoplates or gold nanotriangles having an average size of 200±25 nm and thicknesses not greater than 5 nm. In some embodiments, gold nanoparticles having sizes of not greater than 50 nm, not greater than 25 nm, or not greater than 15 nm.

The probe can include DNA for example. In embodiments where the probe includes DNA, the length of the DNA strand can be such that the strand is long enough that it is selective to the target or analyte of interest. The probe is also of a length, e.g., an actual length, that the plasmonic material-probe complex can form dimers once the target is hybridized to two plasmonic material-probe complexes. Useful probe lengths can range from 10 to 14 bases in the case of DNA or 8 to 10 nm for DNA or other types of probes.

Such methods can determine the presence or absence of the target of interest in the sample based on an increased intensity of a luminescent signal as compared to a sample without the target. Because only aggregated plasmonic material-probe complex causes an increase in the intensity of the luminescent signal and only plasmonic material-probe that is hybridized with the target of interest will cause the plasmonic material-probe complex to aggregate, an increase in luminescent intensity is caused by the presence of a target that hybridizes with the plasmonic material-probe complex, e.g., the target of interest.

Disclosed methods can also include an additional step or steps of extracting the target of interest, e.g., a specific DNA strand, from the combined sample plasmonic material-probe complex.

In some specific illustrative embodiments, nanoparticles can be conjugated to single-stranded DNA probes (to produce AuNPs-DNA as an example of a plasmonic material-probe complex) capable of specifically hybridizing with the complementary regions of the target sequence localized within the genomic DNA of *C. fagacearum*. The molecular recognition of the target based on the sequence-specific DNA hybridization leads to immediate aggregation of the AuNPs. In the presence of luminol (illustrative chemiluminescent agent) and hydrogen peroxide ($H_2O_2$) (illustrative oxidant), such hybridization results in a significant and measurable change in chemiluminescence intensity.

This disclosure is further illustrated by the following examples. It is to be understood that the particular examples, materials, amounts, and procedures are to be interpreted broadly in accordance with the scope and spirit of the disclosure as set forth herein.

Example 1

Materials and Instrumentation

All chemicals and reagents were purchased from Sigma-Aldrich (St. Louis, Mo., USA), and used as received unless otherwise noted. *Escherichia coli* Castellani and Chalmers (ATCC 25922), *Mucor circinelloides* (ATCC® MYA3787™) and Lactobacilus *delbrueckii* subsp. *bulgaricus* (ATCC 11842) were purchased from ATCC, VA, USA. Methicillin-resistant *Staphylococcus aureus* (MRSA) was a generous gift from Dr. Srinand Sreevatsan (Veterinary Population Medicine Department, University of Minnesota). Rabbit anti-MRSA and rabbit anti-Ecoli (O+K) polyclonal antibody were purchased from Abcam Inc., USA. Nanopure water was used for all experiments.

All the chemiluminescent experiments were carried out with the GloMax MultiJR detection and the GloMax® 96 Microplate luminometer system (Promega Corp., WI, USA). Nanoparticles and pathogenic microbes were characterized using a UV-visible spectrophotometer (Shimadzu UV-1800, Shimadzu Corp., USA). Zeta potential was measured using the Stabino zeta potential analyzer (Microtrac, Nikkiso group, USA). Field emission transmission electron microscopy (FE-TEM, FEI Tecnai T12 and FEI Tecnai G2 30 equipped with energy dispersive X-ray (EDX) spectrometer) and field emission scanning electron microscopy (FE-SEM, JEOL 6500 and JEOL 6700) were used for all imaging and atomic characterization. The $^1$H and $^{31}$P NMR were performed on the Agilent/Varian 700SS, 700 MHz and the 6002, 600 MHz (Bruker Corp., USA).

Preparation of Triangular Au Nanoplates (AuNTs)

The triangular shaped Au nanoplates were prepared following previous literature with some modifications (Iranifam M, Imani-Nabiyyi A, Khataee A, Kalantari J. Enhanced luminol-O2 chemiluminescence reaction by CuO nanoparticles as oxidase mimics and its application for determination of ceftazidime. Analytical Methods 2016, 8(18): 3816-3823; and Fulford M R, Walker J T, Martin M V, Marsh P D. Total viable counts, ATP, and endotoxin levels as potential markers of microbial contamination of dental unit water systems. Br Dent J 2004, 196(3): 157-159).

Briefly, the Au nanoplates were prepared in a two-step synthesis. Gold seed solution was made by adding 0.5 mL of 20 mM $HAuCL_4$ solution to 36.5 mL water followed by 1 mL of 10 mM sodium citrate. Then 1 mL of 0.1 M $NaBH_4$ was quickly added to the solution and was stirred for 2 min. The resulting dark orange solution was kept at room temperature for at least 3 hours before use. The growth solution was prepared by making a mixture of 25 mM cetyltrimethylammonium bromide (CTAB, 108 mL) with 20 mM $HAuCl_4$ (1.5 mL), 0.1 M NaOH (600 μL), 0.1 M KI (54 μL) and 0.1 M L-ascorbic acid (600 μL). The growth solution should be transparent after adding L-ascorbic acid. The following steps involved in a multiple-step growth at a specific time and volume. First, 100 μL of seed solution was added to 900 μL of growth solution, mixed well and incubated for 10 min. After 10 min, all the solution was added to 9 mL of growth solution in a glass vial and incubated for another 10 min. After the 10 min incubation, all the solution was added to 92 mL growth solution. The resulting deep purple solution was stored in dark container for another 24 h allowing Au nanoplates to grow along the walls and the bottom of the flask. Then, the supernatant solution was gently poured out and 10 mL of 25 mM CTAB was added to disperse Au nanoplates using pipetting and sonication.

Figure 1F:
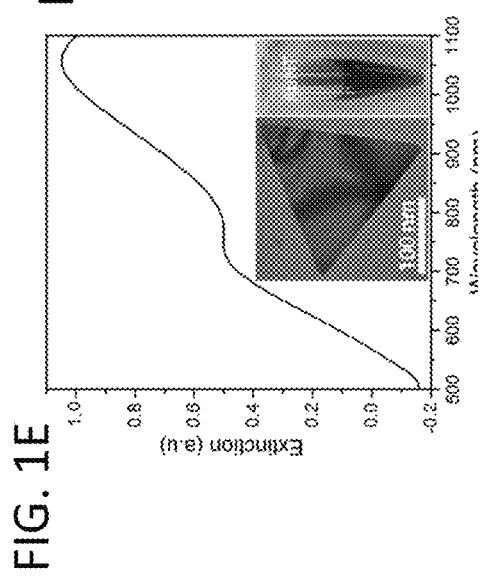
Figure 1H:
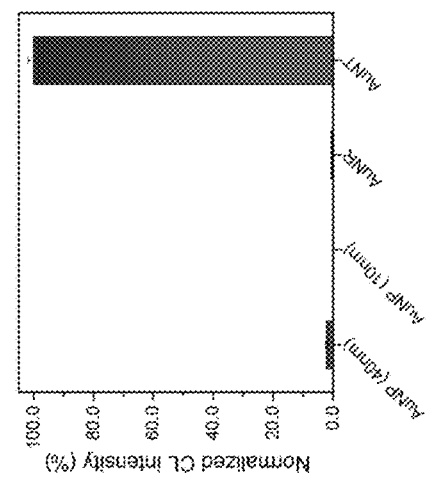
Figure 1G:
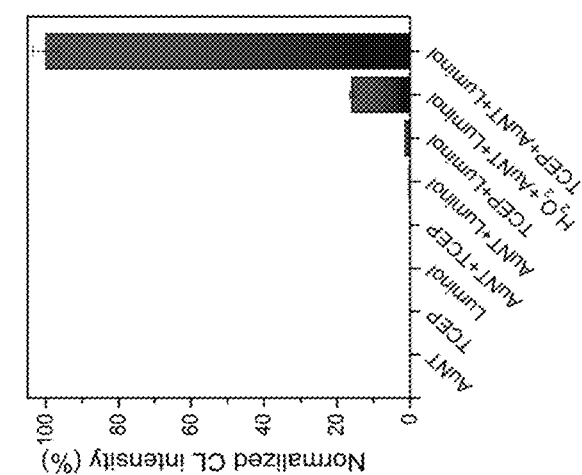
Figure 1I:
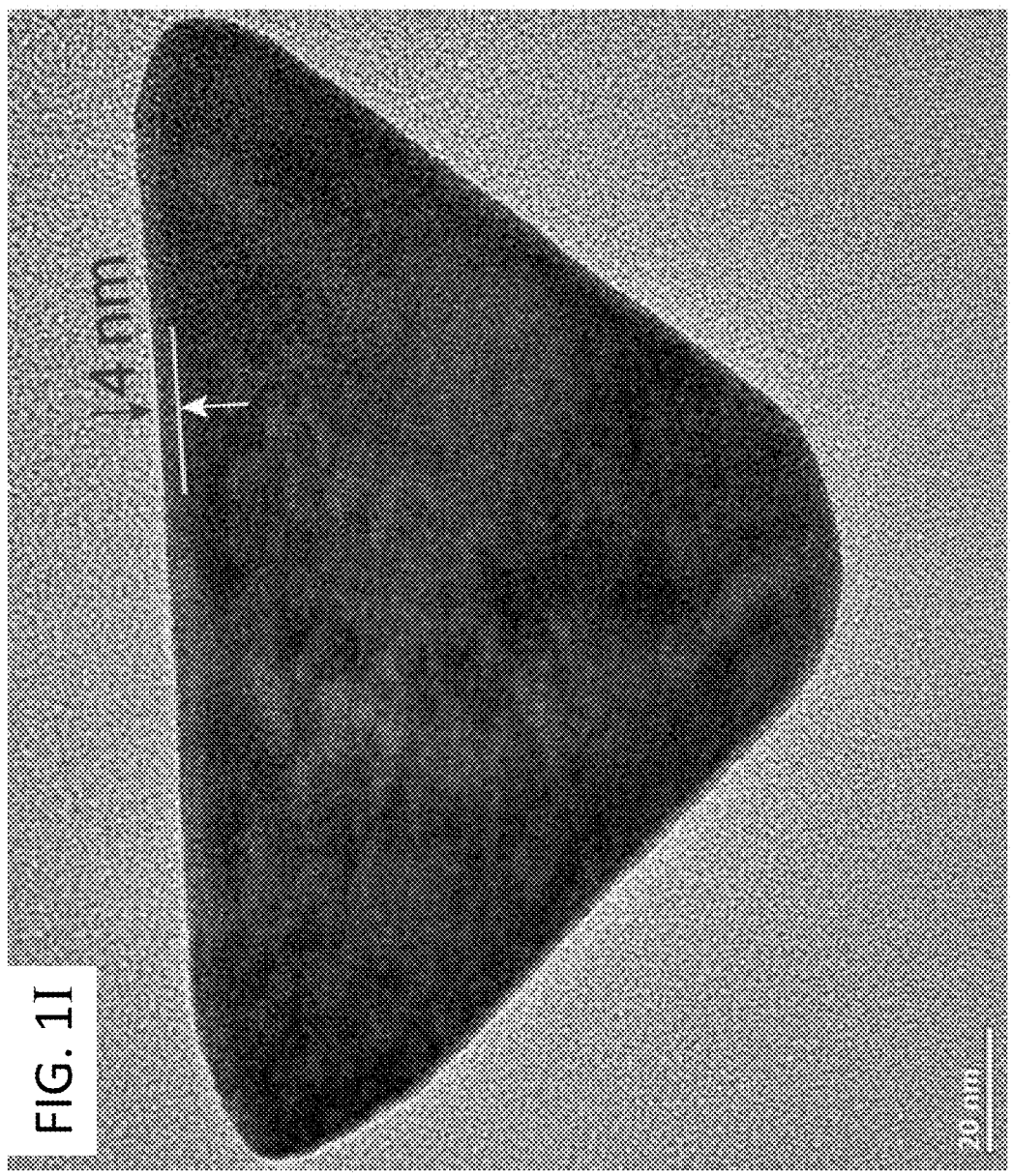
Figure 6:
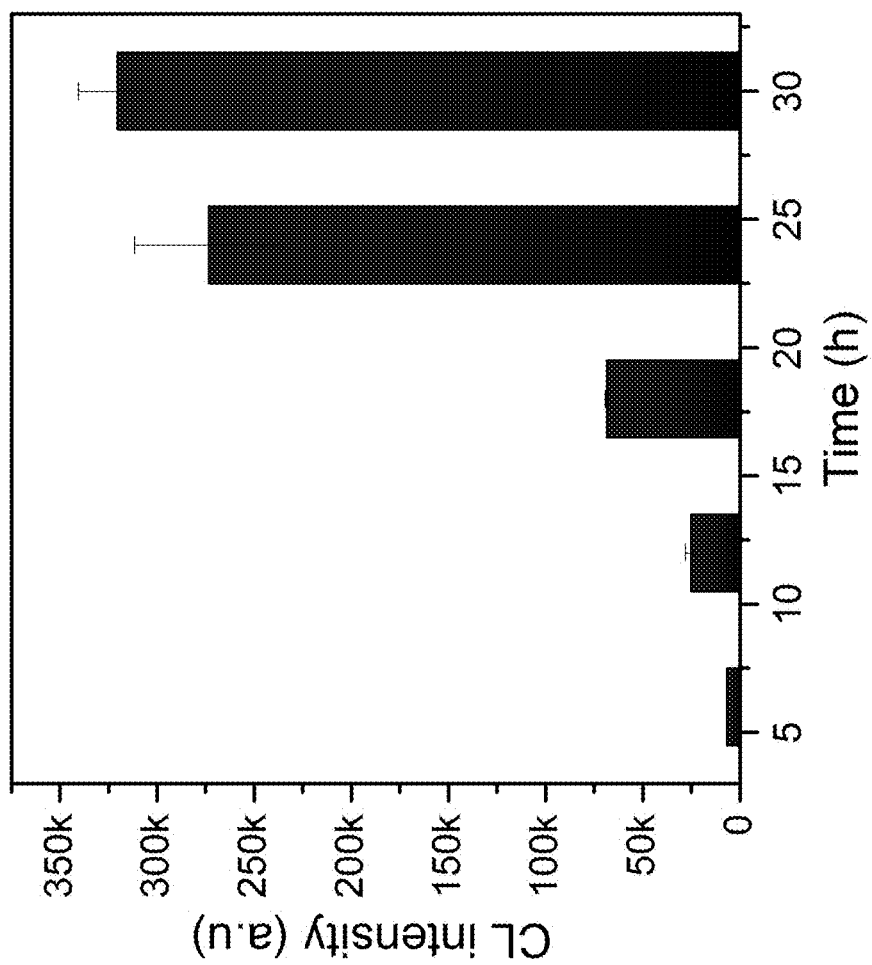
FIG. 6 shows chemiluminescent signal responses at different synthesized time of Au nanoplates (AuNTs).

As depicted in FIG. 1E, the UV-visible spectrum of the synthesized Au nanoplates exhibits two typical absorption peaks at 735 nm and 1055 nm, respectively. The Au nanoplates in 20 mM CTAB solution was visible as an intense green color, triangular in shape and have average size of 200±25 nm as marked in the insets of FIG. 1E. However, the Au nanoplates were thin with an expected thickness in the range of 3-5 nm (FIG. 1I). The high resolution TEM image taken at one edge of Au nanoplates shows distinct lattice planes with a d-spacing of 2.40 nm which was assigned to the {111} planes of the face-centered cubic (fcc) gold (FIG. 1B). The selected area electron diffraction (SAED) pattern of Au nanoplates exhibited a set of six brighter spots, which correspond to the {220} reflections of a fcc single-crystal oriented in the [111] zone axis. Another set of dim spots with hexagonal symmetry within the {220} spots was indexed for the ⅓ {422} reflections indicating the presence of single twinning boundary within the gold {111} planes perpendicular to the electron beam of TEM (Iranifam M, Imani-Nabiyyi A, Khataee A, Kalantari J. Enhanced luminol-O2 chemiluminescence reaction by CuO nanoparticles as oxidase mimics and its application for determination of ceftazidime. Analytical Methods 2016, 8(18): 3816-3823; Fulford M R, Walker J T, Martin M V, Marsh P D. Total viable counts, ATP, and endotoxin levels as potential markers of microbial contamination of dental unit water systems. Br Dent J 2004, 196(3): 157-159; Omidbakhsh N, Ahmadpour F, Kenny N. How Reliable Are ATP Bioluminescence Meters in Assessing Decontamination of Environmental Surfaces in Healthcare Settings? PLoS ONE 2014, 9(6): e99951; Tangeysh B, Moore Tibbetts K, Odhner J H, Wayland B B, Levis R J. Triangular Gold Nanoplate Growth by Oriented Attachment of Au Seeds Generated by Strong Field Laser Reduction. Nano Letters 2015, 15(5): 3377-3382; and Miranda A, Malheiro E, Skiba E, Quaresma P, Carvalho P A, Eaton P, et al. One-pot synthesis of triangular gold nanoplates allowing broad and fine tuning of edge length. Nanoscale 2010, 2(10): 2209-2216). The atomic EDX mapping on the surface of single crystalline Au nanoplates shows typical gold peak (insets of FIG. 1E). Although, the size of Au nanoplates did not increase over different time in the growing step Au nanoplate, the concentration of Au nanoplate increases significant at 24 h of synthesis which was confirmed by UV-vis spectra. As a result, the chemiluminescence intensity was observed to increase rapidly at 24 h of synthesis time and was saturated after 30 h (FIG. 6).

Preparation of the Microbial Suspensions

*Mucor circinelloides* foodborne pathogen (ATCC® MYA-3787™) and *Escherichia coli* Castellani and Chalmers (ATCC 25922) were grown in tryptic soy agar medium. *Lactobacillus delbrueckii* subsp. *bulgaricus*. (ATCC 11842) were grown on the DeMan-Rogosa-Sharpe Agar media. Methicillin-resistant *Staphylococcus aureus* (MRSA-SP19 and MRSA-PP7) were grown on the brain heart infusion agar and incubated at 37° C. for 1 day. The cultures were stored at 4° C. until use. All kind of media for microbial culture above were purchased from Sigma-Aldrich. Each sample was suspended and diluted in nanopure water to the value of 0.2 absorbance at 600 nm The suspension was then serial ten-fold diluted to different concentrations in nanopure water. The microbial concentrations were confirmed using the BD Accuri™ C61 flow cytometer (BD Biosciences, USA) and plate counting.

Conjugation of Antibody to Macromolecular Polymer.

The 0.5% w/v solution of NHS-PEG-2000 was prepared in 10 mM phosphate saline buffer, pH 7.4 before conjugate to anti-rabbit IgG. Briefly, 500 µL of 100 µg/mL anti-rabbit IgG antibody was added to 4.5 mL of the above NHS-PEG-2000 polymer solution and incubate for 15 minutes at room temperature with stirring. The solution was then further incubated at 4° C. for another 8 hours. Similarly, EDC-NHS cross-linker was used to conjugate chitosan polymer with anti-rabbit IgG. 0.5% w/v chitosan solution (MW ~190 kDa) was prepared in acetate buffer and adjusted to pH 5.5. For the conjugation of the anti-rabbit IgG to the chitosan polymer, 200 µL of 1 mg/mL anti-Rabbit IgG was added to 300 µL of EDC (1% w/v) solution and incubated for 5 min. Then, 300 µL of NHS (2% w/v) was added.[23] The mixture was vortexed, mixed well and incubated for 15 minutes at room temperature. The solution was then mixed to 5 mL of chitosan solution, incubated at room temperature for 1 hour with stirring. All the conjugated solutions were dialyzed overnight in PBS buffer through dialysis membrane with MWCO of 7000 Da to remove non-conjugated antibodies.

Microbial Screening

Luminol solution (0.2 mg/mL) and 10 mM tris(2-carboxyethyl)phosphine hydrochloride (TCEP) were freshly prepared before use. The CTAB surfactant in the Au nanoplates solution was removed after synthesis by centrifuging at 8000 rpm for 10 minutes, the supernatant was discarded and the Au nanoplates were suspended in nanopure water. For microbial screening, to the Eppendorf, 100 µL of sample solution was mixed to 30 µL of 10 mM TCEP and incubated for 5 minutes at room temperature. Then, 100 µL of Au nanoplates solution ($OD_{750\ nm}$=0.5) was added to the mixture followed by 100 µL of luminol solution. The CL intensity was measured using 10 s interval for a period of 5-10 minutes. Control samples were performed using either nanopure water or 10 mM PBS buffer, pH 7.4.

For urine test, different concentration *E. coli* was spiked to 1 mL of urine samples. Then, the samples were centrifuge twice at 13,000 rpm in 10 min. The supernatant was removed and re-suspended in 100 µL water before testing following the same procedure above. The CL intensity was collected and each sample was repeat at least 3 times to get average signal and standard deviation value.

Specific Identification of Pathogenic Bacteria.

The in vitro testing for specific detection of MRSA pathogenic bacteria was performed in the BSL level 2 laboratory. All of the bacteria were growth in appropriate media, temperature and time to obtain visible colonies. Before testing, each type of pathogenic bacteria's colonies was dissolved in 10 mM PBS buffer, pH 7.4. A serial ten-fold dilution of each samples was performed from the bacteria stock solutions at $OD_{600\ nm}$=1.0. The concentration of bacteria was also confirmed by flow cytometry and plated counting as in our previous report.[31] For specific MRSA identification, 25 µL of each sample solution (100 µL total) was added to the Eppendorf followed by 20 minutes incubation with 50 µL of rabbit anti-MRSA-IgG polyclonal antibodies (100 µg/mL) diluted in PBS buffer from stock solution. Then, 50 µL of anti-rabbit IgG conjugated PEG was added to the mixture and incubated for another 20 minutes. After that, 30 µL of 10 mM TCEP solution was added to the solution and incubated for 5 minutes before adding 100 µL of Au nanoplates and 100 µL of luminol (0.2 mg/mL) to the mixture for generating chemiluminescence signal. The chemiluminescence intensity was measured immediately on the portable Glomax® luminometer. The kinetics of CL profiles were collected for 5 minutes and analyzed in Origin Pro v9.1 (Originlab Corp. USA). The controlled experiments were also performed in the absent of either pathogenic bacteria or anti-MRSA-IgG antibody or conjugated PEG polymer with PBS buffer, pH 7.4.

Cotton swab tests were performed on the laboratory's bench using the mixture of E. coli ($10^3$ cfu·$ml^{-1}$) and MRSA-PP7 ($10^4$ cfu·$ml^{-1}$) in nanopure water. The cottons were swabbed and re-dispersed in 100 µL of water follow by the testing procedure as described above for specific detection of MRSA. Control samples and non-shielding tests were performed by replacing either samples or anti-MRSA antibodies with PBS buffer, pH 7.4.

Example 2

The reduction of disulfide bonds on the microbial surface by TCEP along with the addition of gold nanoparticles (AuNPs) had been previously reported. That work resulted in cell nanocoating of the microorganisms with thin AuNPs layers. The use of chemiluminescence to detect the aggregation of the AuNPs on the microbial surface, was then studied. It was assumed that the chemiluminescence would have been affected by a change in nanoparticle distribution. It has been known that catalytic activities, physicochemical and optoelectronic properties of metal and semiconductor nanoparticles are not only size dependent but also shape dependent (Rao C N R, Kulkarni G U, Thomas P J, Edwards P P. Size-Dependent Chemistry: Properties of Nanocrystals. Chemistry—A European Journal 2002, 8(1): 28-35; Narayanan R, El-Sayed M A. Shape-Dependent Catalytic Activity of Platinum Nanoparticles in Colloidal Solution. Nano Letters 2004, 4(7): 1343-1348; Mostafa S, Behafarid F, Croy J R, Ono L K, Li L, Yang J C, et al. Shape-Dependent Catalytic Properties of Pt Nanoparticles. Journal of the American Chemical Society 2010, 132(44): 15714-15719; Zhou X, Xu W, Liu G, Panda D, Chen P. Size-Dependent Catalytic Activity and Dynamics of Gold Nanoparticles at the Single-Molecule Level. Journal of the American Chemical Society 2010, 132(1): 138-146; and Zeng J, Zhang Q, Chen J, Xia Y. A Comparison Study of the Catalytic Properties of Au-Based Nanocages, Nanoboxes, and Nanoparticles. Nano Letters 2010, 10(1): 30-35). Thus, it was hypothesized that using gold nanotriangles instead of nanoparticles would further improve the enhancement due to the catalytic effect of their sharp angles in chemical reactions. Triangular Au nanoplates (AuNTs) with an average size of 200±25 nm and thicknesses below 5 nm have been synthesized and characterized (FIGS. 1A, 1E). However, when mixing the Au nanoplates with a reduced microbial sample, not only was no aggregation observed, but in fact a strong enhancement of the luminol chemiluminescence signal was observed (FIG. 1D). SEM images confirmed the absence of microbial cell nanocoating with the nanoplates. To understand the origin of the enhancement, TCEP was replaced with other reducing agents such as beta-mercaptoethanol (BME), dithiothreitol (DTT) or sodium borohydride (NaBH4). Only TCEP had an effect on luminol chemiluminescence signal in the presence of Au nanoplates (FIG. 1F). When mixing luminol with either TCEP or Au nanoparticles, no signal enhancement was observed (FIG. 1G), suggesting that the enhancement effect results from the interaction of TCEP with Au nanoplates. Replacing Au nanoplates with gold nanoparticles or gold nanorods significantly drops the CL signal by over 95%, indicating the important role of Au nanoplates (FIG. 1H).

The Catalytic Effect of TCEP/Au Nanoplates on Chemiluminescence

One feature of the TCEP-nanoplate-luminol system is the luminescence stability over a relatively long period of time. In conventional chemiluminescence systems, metal nanoparticles such as gold or silver nanoparticles and metal nanoclusters such as copper, cobalt and Zn/Cu@BSA (bovine serum albumin) have been employed to accelerate the kinetics and to improve the CL quantum yield due to their high catalytic activity (Chen H, Lin L, Li H, Li J, Lin J-M. Aggregation-Induced Structure Transition of Protein-Stabilized Zinc/Copper Nanoclusters for Amplified Chemiluminescence. ACS Nano 2015, 9(2): 2173-2183; Aslan K, Geddes C D. Metal-enhanced chemiluminescence: advanced chemiluminescence concepts for the 21st century. Chemical Society Reviews 2009, 38(9): 2556-2564; and Li Q, Liu F, Lu C, Lin J-M. Aminothiols Sensing Based on Fluorosurfactant-Mediated Triangular Gold Nanoparticle-Catalyzed Luminol Chemiluminescence. The Journal of Physical Chemistry C 2011, 115(22): 10964-10970). For instance, in the presence of Cu(II) or Co(II) as catalysts, luminol reaction with hydrogen peroxide causes instantaneous emission that reaches a maximum within a few seconds (Yeh H-C, Hsu W-T, Lin W-Y. Enhancement in Chemiluminescence by Carbonate for Cobalt(II)-catalyzed Oxidation of Luminol with Hydrogen Peroxide. Journal of the Chinese Chemical Society 2005, 52(4): 657-664; and Khan P, Idrees D, Moxley M A, Corbett J A, Ahmad F, von Figura G, et al. Luminol-Based Chemiluminescent Signals: Clinical and Non-clinical Application and Future Uses. Appl Biochem Biotechnol 2014, 173(2): 333-355). However, the light intensity decays to approximately 50% in about 8 seconds and the signal is highly dependent on Cu(II) concentration. As shown in FIG. 1B, the mixture of TCEP and luminol in the presence of Au nanoplates, generated a luminescence intensity that reached a maximum in about 5 min and was stable for over 10 min, which provides sufficient time to perform any sample analysis. The long-term emission may be the result of a continuous oxidation of the Au nanoplates by TCEP until all the nanoplates are etched. This is likely made possible by the extremely small thickness of the Au nanoplates, ranging from 3 to 5 nm only (FIG. 1I), which is known to offer optimal gold catalytic activity (Turner M, Golovko V B, Vaughan O P H, Abdulkin P, Berenguer-Murcia A, Tikhov M S, et al. Selective oxidation with dioxygen by gold nanoparticle catalysts derived from 55-atom clusters. Nature 2008, 454(7207): 981-983; and Comotti M, Della Pina C, Matarrese R, Rossi M. The Catalytic Activity of "Naked" Gold Particles. Angewandte Chemie International Edition 2004, 43(43): 5812-5815). Furthermore, the large size of the nanoplates (200 nm) provide large surface area, which further enhances the efficiency A second feature of disclosed methods are that the oxidation of Au nanoplates by TCEP is concentration-dependent. FIG. 2A depicts TEM images of Au nanoplates after interaction with different concentrations of TCEP in the presence of luminol, showing that the nanoplates are increasingly etched at all planes. Nanoplate oxidation increases by increasing TCEP concentration up to a certain level, translated by an increase in CL signal enhancement (FIG. 2B). The CL intensity reaches its maximum level at a TCEP concentration around 1.35 mM, where the Au nanoplates are largely etched, fused and formed aggregates (FIG. 2A-e). However, at TCEP concentrations higher than 1.67 mM, the stabilizer on the Au nanoplates surface, CTAB, seems to be rapidly disrupted, prompting nanoplate agglomeration and stacking without etching (FIG. 2A-f). The Au nanoplates were stacked together, thus significantly reducing the accessibility of TCEP to the large facets of the nanoplates, limiting oxidation and decreasing the chemiluminescence signal.

Reaction Mechanism: The Interaction of TCEP with Au Nanoplates and Luminol

To understand the mechanism of the chemiluminescence enhancement, the reaction medium was analyzed using nuclear magnetic resonance (NMR). $^1$H and $^{31}$P NMR spectra of TCEP, luminol, Au nanoplates and their mixtures were obtained and analyzed. As shown in FIG. 3A, the $^1$H-NMR spectra of TCEP (spectrum 1) was right-shifted with a value of 0.62 and 0.89 ppm after its interaction with either luminol (spectrum 2), Au nanoplates (spectrum 3) or a mixture of both (spectrum 4). This suggests that TCEP was reduced after receiving electrons from Au nanoplates and luminol (Chen S, Jiang H, Wei K, Liu Y. Tris-(2-carboxyethyl) phosphine significantly promotes the reaction of cisplatin with Sp1 zinc finger protein. Chemical Communications 2013, 49(12): 1226-1228). The substituted phosphine group of TCEP showed a strong peak at 16.1 ppm (FIG. 3b) (Krczel A, Latajka R, Bujacz G D, Bal W. Coordination Properties of Tris(2-carboxyethyl)phosphine, a Newly Introduced Thiol Reductant, and Its Oxide. Inorganic Chemistry 2003, 42(6): 1994-2003). Broader $^{31}$P peak could be observed in the mixture of TCEP, luminol and Au nanoplates indicating an electron movement around the phosphor atom of TCEP (spectrum 4).

Figure 4:
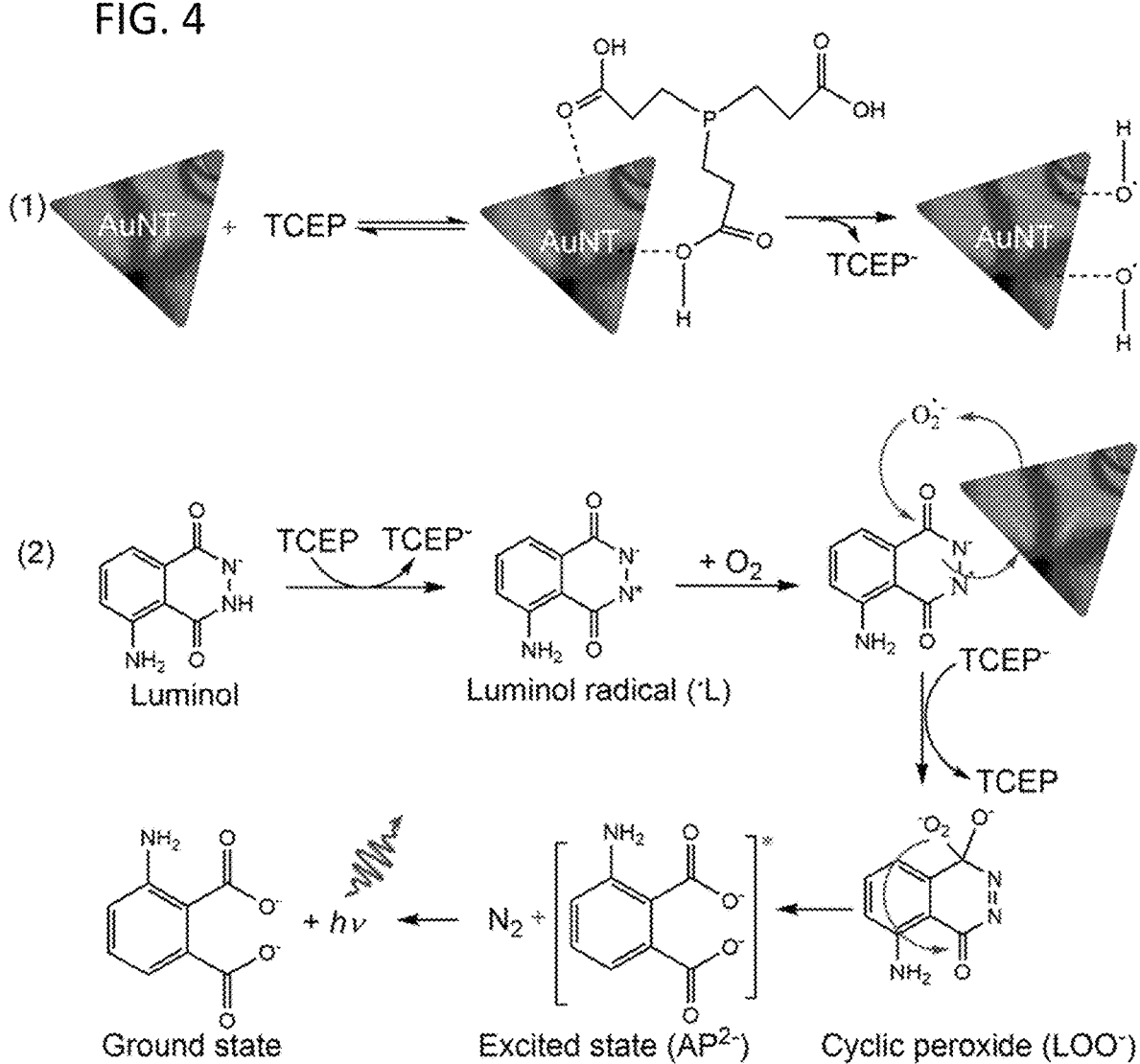
FIG. 4 is a schematic illustration of the chemiluminescent mechanism of TCEP, luminol and Au nanoplates.

The proposed mechanism of the reaction of TCEP with luminol and Au nanoplates is illustrated in FIG. 4. First, the anionic form of TCEP in aqueous solution comes into contact with the Au nanoplates (AuNT), where it acts as an oxidant to generate the key intermediate hydroxyl radical (0.0H) on the surface of the Au nanoplates (AuNT) (reaction 1). This oxidation reaction occurs continuously on the surface of Au nanoplates until all the Au nanoplates are consumed or become inaccessible (Duan C, Cui H, Zhang Z, Liu B, Guo J, Wang W. Size-Dependent Inhibition and Enhancement by Gold Nanoparticles of Luminol-Ferricyanide Chemiluminescence. The Journal of Physical Chemistry C 2007, 111(12): 4561-4566; and Millstone J E, Hurst S J, Métraux G S, Cutler J I, Mirkin C A. Colloidal Gold and Silver Triangular Nanoprisms. Small 2009, 5(6): 646-664). Simultaneously, luminol in basic condition undergoes deprotonation of the —NH—NH— group. The subsequent oxidation of luminol by TCEP generates the luminol radical (•L). During this reaction, the reduced form of TCEP (TCEP$^-$) was also generated as confirmed by the $^1$H-NMR (reaction 2), suggesting an electron transfer from luminol to TCEP.

The oxidation of both nanoplates (AuNT) and luminol by TCEP generates respectively hydroxyl radical (•OH) and luminol radical (•L). In the presence of oxygen, the hydroxyl radical (•OH) produces singlet oxygen (•O$_2$—), leading to the oxidation of luminol radical (•L). The latter is then reduced by TCEP$^-$ to generate instable hydroxyl hydroperoxide (LOO$^-$), which rapidly decomposes to form the excited state of luminol (AP$_2$—). The change of electrons from the excited state to the ground state releases energy, causing light emission at 425 nm. Although, chemiluminescence is a flash phenomenon in the millisecond time scale (Duan C, Cui H, Zhang Z, Liu B, Guo J, Wang W. Size-Dependent Inhibition and Enhancement by Gold Nanoparticles of Luminol-Ferricyanide Chemiluminescence. The Journal of Physical Chemistry C 2007, 111(12): 4561-4566.; and Iranifam M, Imani-Nabiyyi A, Khataee A, Kalantari J.

Enhanced luminol-O2 chemiluminescence reaction by CuO nanoparticles as oxidase mimics and its application for determination of ceftazidime. Analytical Methods 2016, 8(18): 3816-3823), the use of thin Au nanoplates and TCEP continuously supplies oxygen singlet to the chemiluminescence reaction, enabling a stable long-term emission.

The Interaction of TCEP with Microorganisms

Figure 5D:
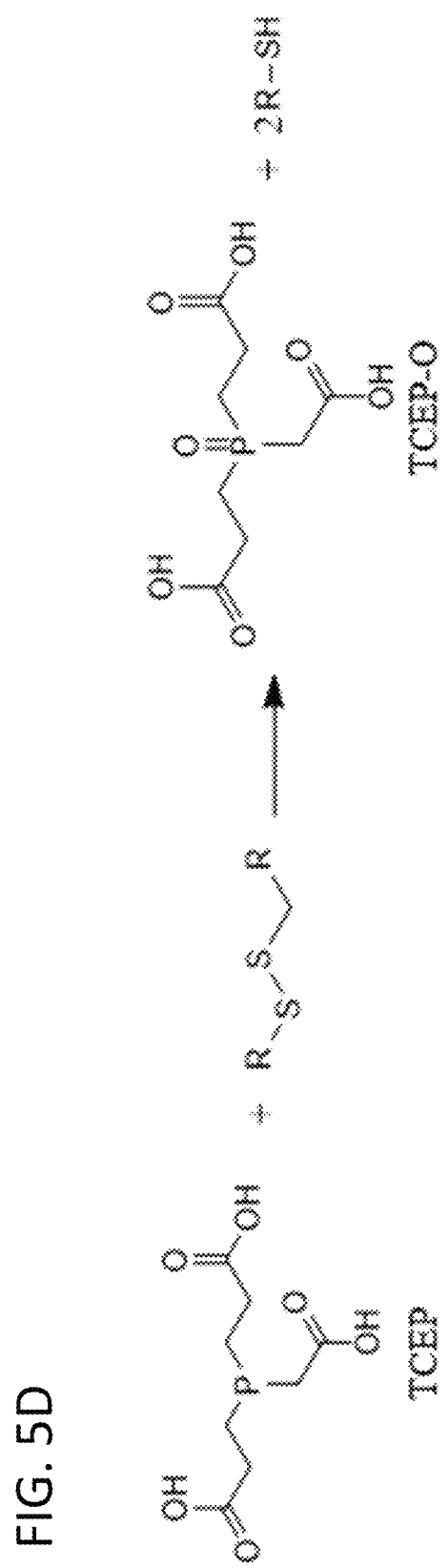
FIG. 5D shows a schematic of TCEP attach on disulfide bridge to generate free thiol group and oxidation form of TCEP (TCEP-O).

As discussed above, TCEP leads to a strong luminescence enhancement in the presence of Au nanoplates. However, in the presence of microorganisms, the enhancement effect decreased proportionally to the microbial concentration. It is known that TCEP reduces the disulfide bond on the Dsbc proteins present on the microbial outer layers. To understand this effect, $^1$H and $^{31}$P NMR were used to analyze the structure of TCEP after interaction with *Escherichia coli* (*E. coli*) as a model microorganism. The results were compared to TCEP oxidized using hydrogen peroxide. As shown in FIG. 5A, oxidized TCEP (TCEP-O) obtained after hydrogen peroxide treatment exhibit two specific $^1$H NMR peaks at 2.55 and 2.10 ppm (curve 1). The interaction of TCEP with *E. coli* results in the appearance of the same peaks (curve 2), indicating the partial conversion of TCEP into its oxidized form, TCEP-O, after reduction of the disulfide bond on the microbial surface (FIG. 5B). The $^{31}$P NMR spectra in FIG. 5C also confirmed the formation of new P═O peak at 56.2 ppm in TCEP-O structure (spectrum 1) along with the P—H bond peak at 16.1 ppm assigned to TCEP (spectrum 2) (Chen S, Jiang H, Wei K, Liu Y. Tris-(2-carboxyethyl) phosphine significantly promotes the reaction of cisplatin with Sp1 zinc finger protein. Chemical Communications 2013, 49(12): 1226-1228). It's important to note that the oxidation of TCEP is irreversible and yields a stable and non-reactive TCEP-O product (Krczel A, Latajka R, Bujacz G D, Bal W. Coordination Properties of Tris(2-carboxyethyl)phosphine, a Newly Introduced Thiol Reductant, and Its Oxide. Inorganic Chemistry 2003, 42(6): 1994-2003). This is an important aspect as it allows the quantitative correlation between available oxidized TCEP concentration and the microbial concentration (FIG. 5D).

Chemiluminescence Assay for Rapid Microbial Screening

To demonstrate the use of a disclosed chemiluminescence system for rapid microbial screening and quantification of the microbial load, serial ten-fold dilutions of *E. coli* solutions ($10^1$-$10^9$ cfu·mL$^{-1}$) were prepared in nanopure water. The bacterial concentrations were also confirmed using flow cytometry and plate counting. The microbial suspensions were treated with TCEP (1.35 mM) for 5 min, before adding Au nanoplates (AuNTs) then luminol (0.2 mg·mL$^{-1}$). The mixture was immediately analyzed using a portable GloMax Multi JR luminometer at 10 s interval readings for 5 min. Control experiments were performed in the same conditions by replacing the bacterial suspensions with nanopure water. Each test was performed at least 3 times to obtain average intensity values.

Figures 7A, 7B:
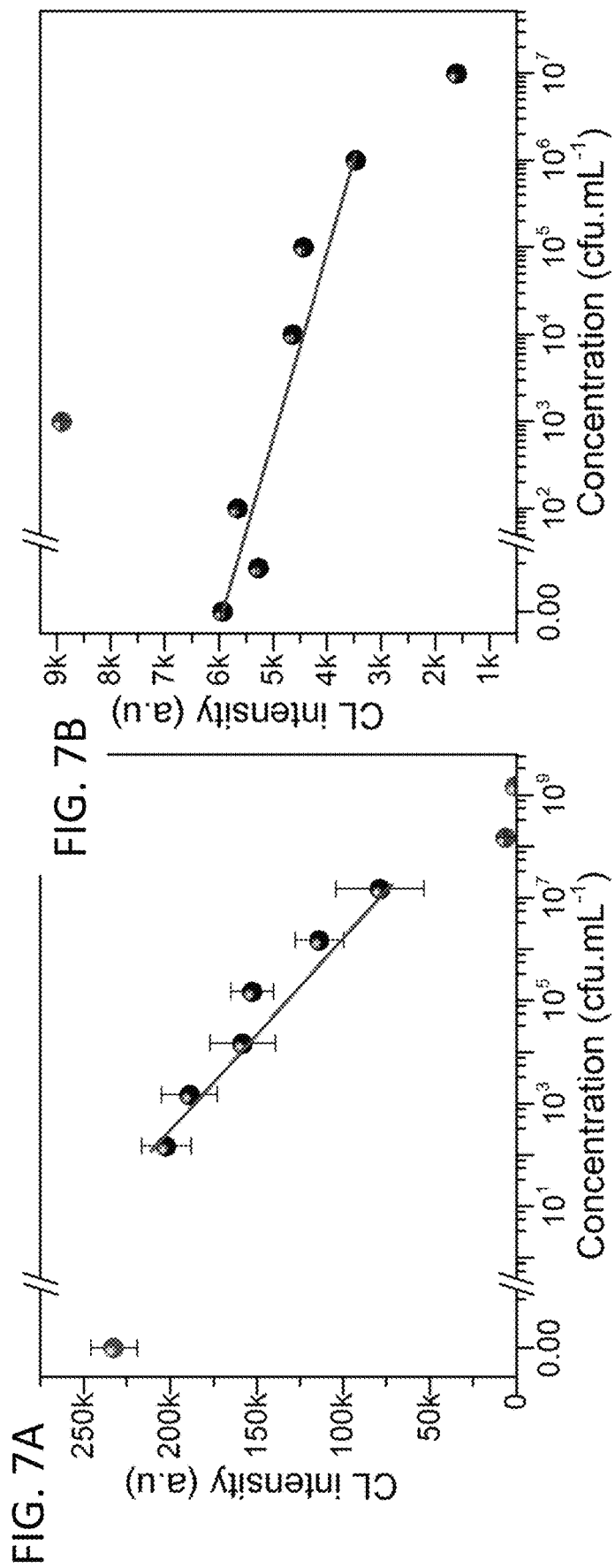
FIGS. 7A, 7B and 7C show calibration plot of chemiluminescence intensity vs E. coli concentration using our developed screening method performed in a portable luminometer (FIG. 7A); 96 well-plate luminometer (FIG. 7B) system; and a flow-injection luminometer system (FIG. 7C).
Figure 7C:
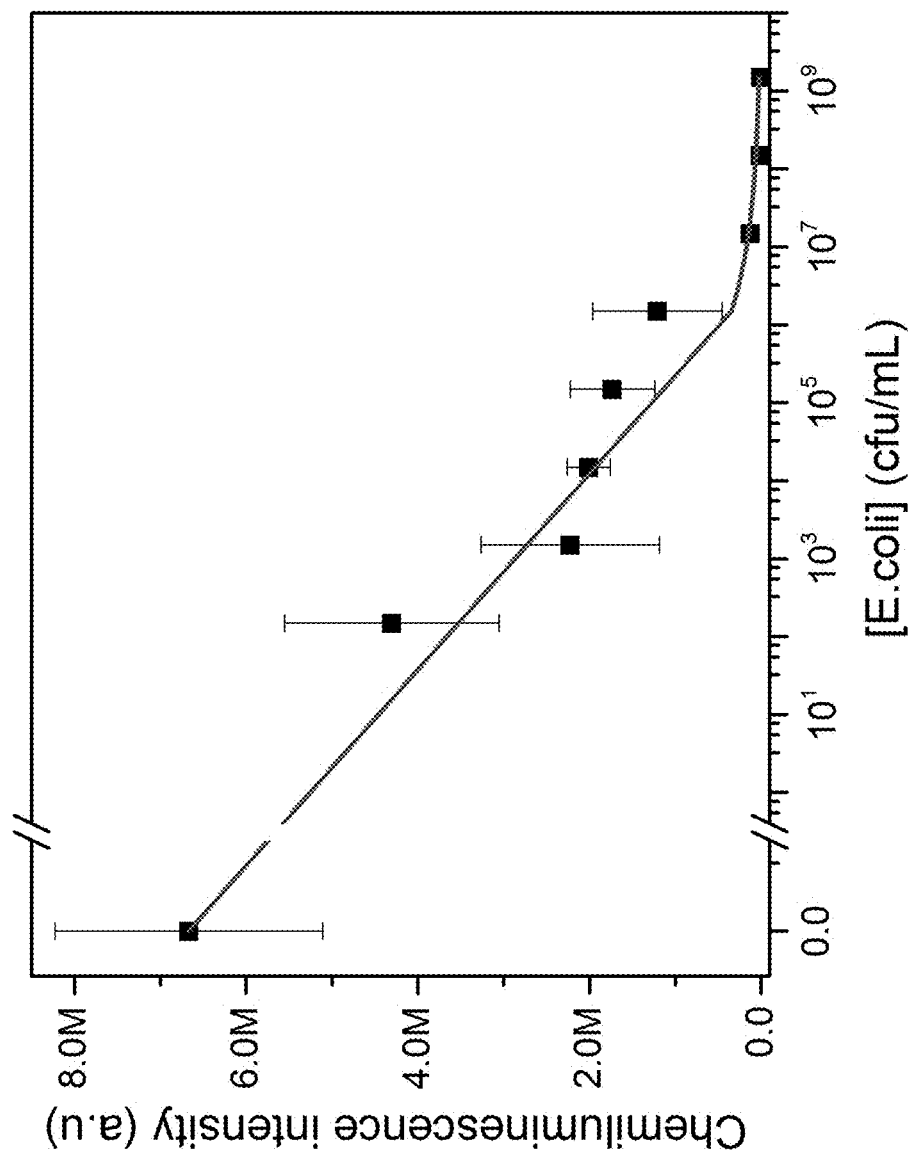

As shown in FIGS. 7A and 7B, *E. coli* concentrations as low as 100 cfu·mL$^{-1}$ can be detected with a linear range of $10^2$—$10^7$ cfu·mL$^{-1}$ ($R^2$=0.97). Similar limit of detection can also be achieved on the 96-well plate using a flow injection luminometer, showing the reproducibility of the detection concept with two different instruments (FIG. 7C). It is worth noting that the whole detection process on environmental samples takes less than 10 minutes, without pre-concentration of the samples or heavy instrumentation. The limit of detection obtained here is 2-4 orders of magnitude lower than commercial chemiluminescence tests that rely on ATP detection (Fulford M R, Walker J T, Martin M V, Marsh P D. Total viable counts, ATP, and endotoxin levels as potential markers of microbial contamination of dental unit water systems. Br Dent J 2004, 196(3): 157-159; and Omidbakhsh N, Ahmadpour F, Kenny N. How Reliable Are ATP Bioluminescence Meters in Assessing Decontamination of Environmental Surfaces in Healthcare Settings? PLoS ONE 2014, 9(6): e99951). Additionally, the proposed concept allows direct detection of microorganisms through their Dsbc surface protein layers instead of detecting microbial byproducts such as ATP, which usually leads to significant rate of false positive due to the presence of ATP independently from the presence of microorganisms. The analysis of more complex samples requires prior dilution or filtration of the sample. Urine samples spiked with different concentrations of E. coli bacteria from 10 to $10^8$ cfu·mL$^{-1}$ were centrifuged twice to remove interfering components before chemiluminescence testing. While the urine sample slightly affects the linear range, the assay provides the same detection limit around 100 cfu·mL$^{-1}$ (FIG. 7B).

Specific Microbial Identification by Macromolecular Shielding

Figure 8A:
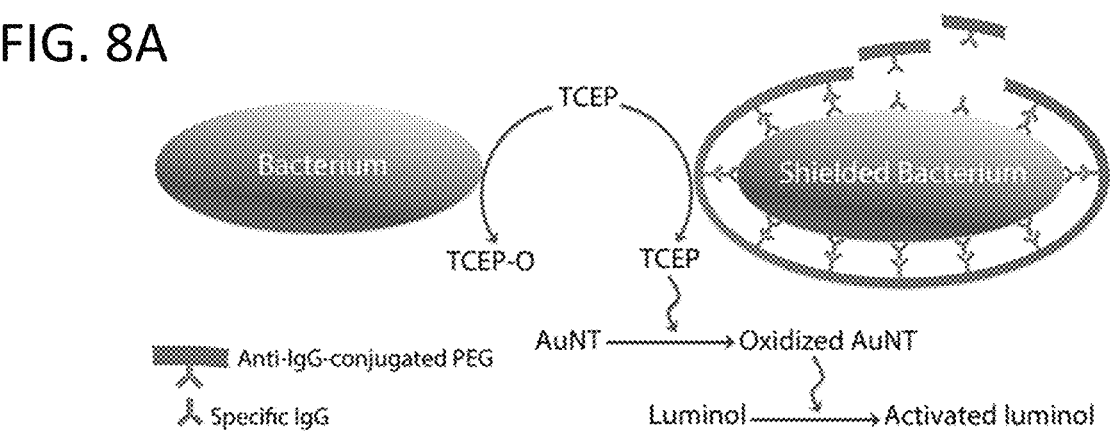
FIGS. 8A, 8B and 8C show a schematic of the interaction of TCEP with shielded and non-shielded bacteria (FIG. 8A); TEM images of (a) PEG polymer, E. coli before (b) and after incubated with anti-Rabbit IgG conjugated-PEG (c) and after incubated with Rabbit anti-E. coli IgG followed by anti-Rabbit IgG conjugated PEG (d)-(k) (FIG. 8B); the analytical performance of the specific disclosed chemiluminescence system in urine spike E. coli samples (FIG. 8C); Zeta potential (column) and pH solution (line) of different microbial samples and the conjugated IgG with chitosan and polyethylene glycol polymer (FIG. 8D); and CL signal kinetic showing the effect of shielding vs non-shielding method using conjugated PEG polymer in 10 mM PBS buffer, pH 7.4 (FIG. 8E).
Figure 8B:
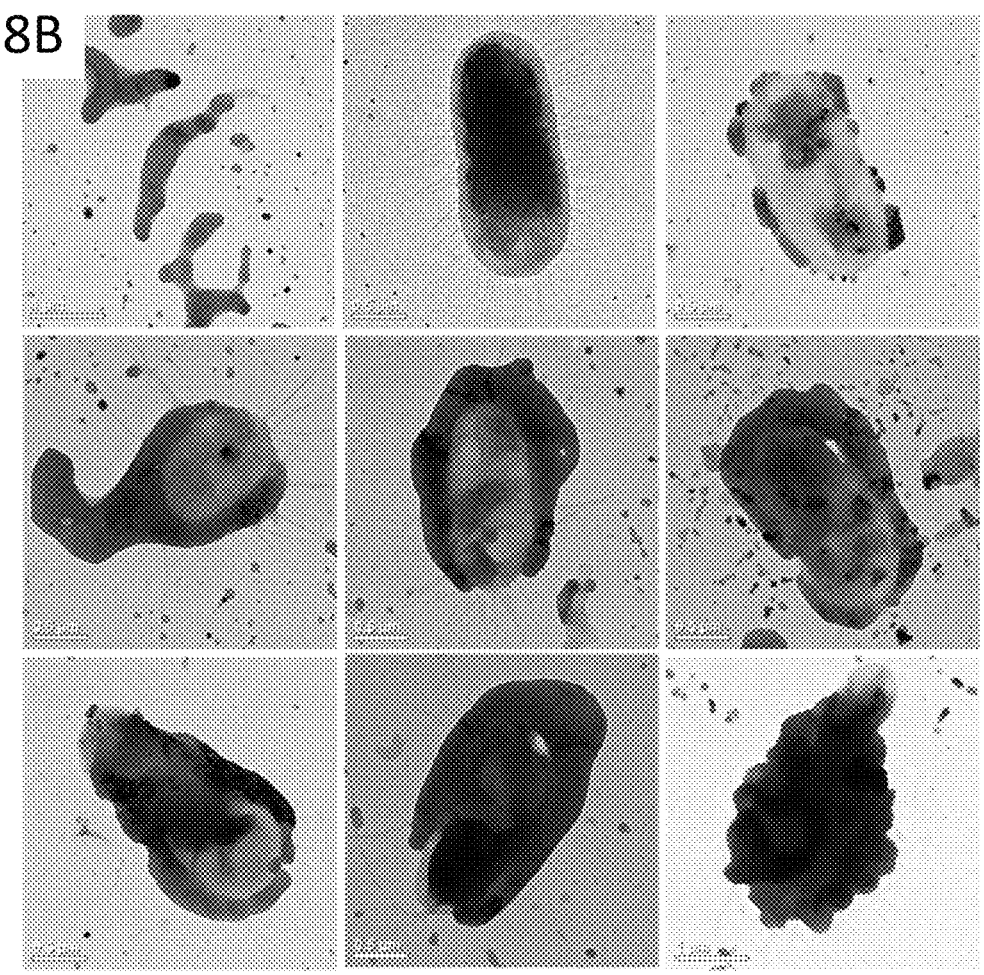
Figure 8C:
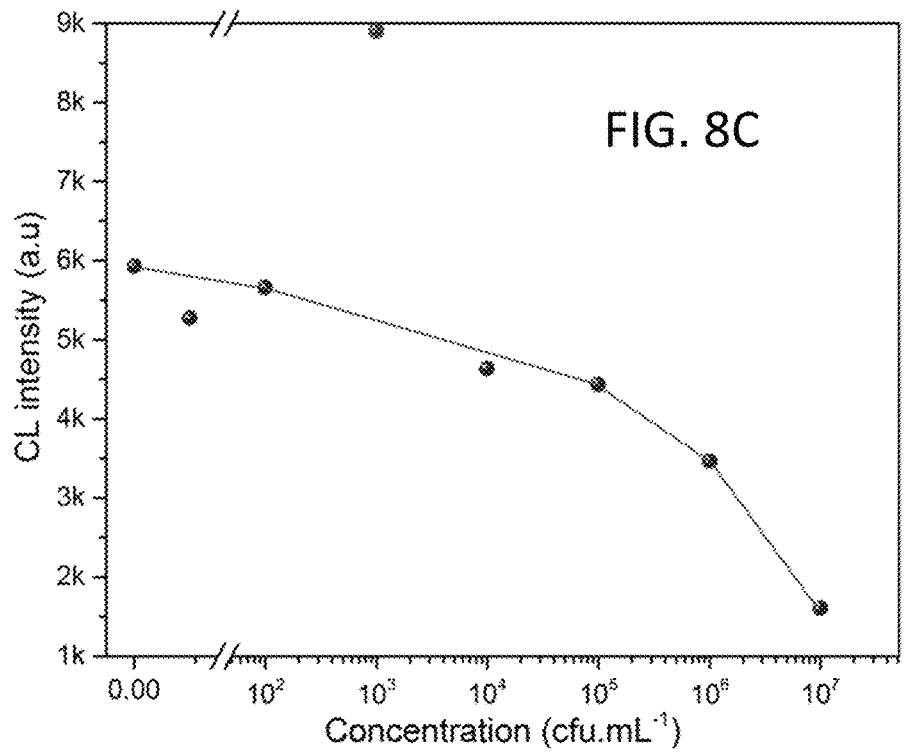
Figure 8D:
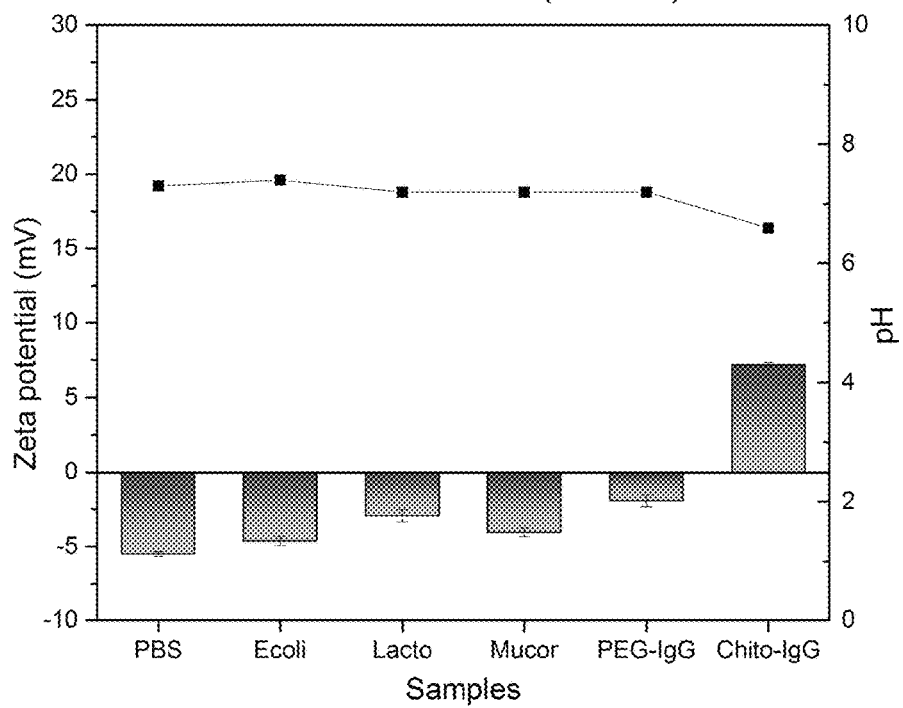
Figure 8E:
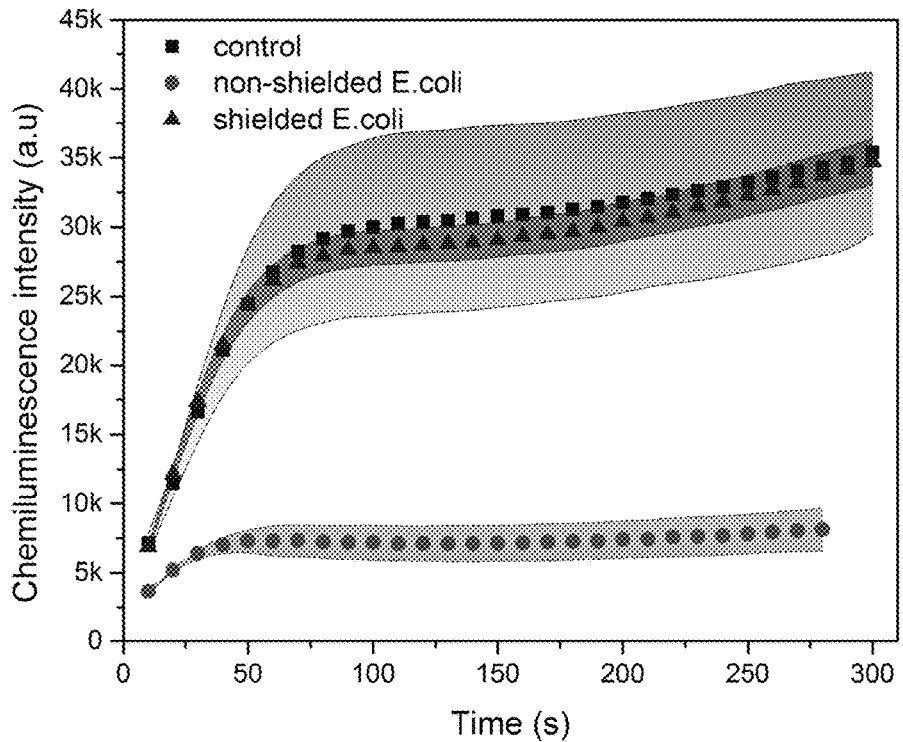

Microbial screening is an important step to evaluate the microbial load and inform decision making for further analysis. However, in a large number of applications, specific identification of the microbial species or strain is needed. To enable microbial identification with the new chemiluminescence system we decided to create a macromolecular shield that specifically covers the target microorganism and prevents it from reduction by TCEP. Such protection would make more TCEP available for interaction with Au nanoplates, leading to an increase in chemiluminescence intensity as detailed earlier. To induce microbial macromolecular shielding on specific bacteria, specific antibodies were added to microbial suspensions, followed by the addition of polyethylene glycol (PEG-2000) polymers conjugated with anti-IgG antibodies (anti-IgG-PEG) (FIG. 8A). After the recognition of the bacteria by the specific antibodies, anti-IgG-PEG spontaneously forms a stable layer around the target microorganism, providing a shielding effect from TCEP reduction of the microbial Dsbc surface proteins. FIG. 8B shows TEM images of E. coli Castellani and Chalmers before and after interaction with the anti-IgG-PEG polymer. The figure clearly shows the progressive shielding of the bacteria until it is completed covered by the polymer in less than 30 min. (FIG. 8B-(d) to (k)). In the absence of the primary (specific) antibody or the secondary (anti-IgG) antibody, the polymer did not interact with the bacteria. In addition, it's interesting to note that there is no non-specific interaction, which is explained by the fact that the zeta potential of the microbial suspensions in PBS buffer ranges from −5 mV to −4 mV, while anti-IgG-PEG shows a value of −2 mV (FIG. 8C). Thus, both bacteria and anti-IgG-PEG exhibit a negative charge, causing electrostatic repulsion and preventing non-specific shielding of the bacteria. In contrast, when PEG is replaced with anti-IgG-chitosan that has a zeta potential around +7 mV, non-specific microbial shielding can occur (FIG. 8D). It is worth noting here that buffer media can have an effect on both the luminescence signal and the efficiency of the microbial macromolecular shielding. A 10 mM PBS buffer at pH 7.4 seems to provide the best performance (FIG. 8E).

Figure 9A:
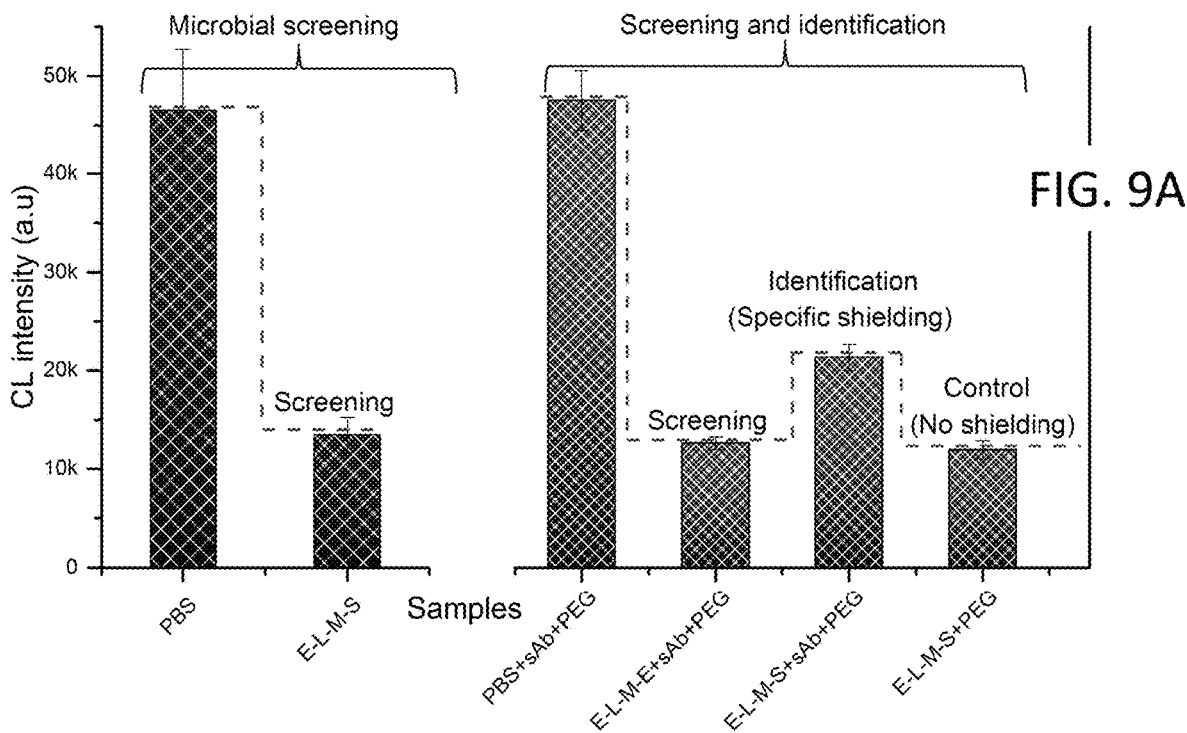
FIGS. 9A and 9B show chemiluminescent measurement using the specific disclosed method in a mixture of four samples including Escherichia coli Castellani and Chalmers (E), Lactobacillus delbrueckii subsp. Bulgaricus (L), Mucor circinelloides (M), and MRSA-SP19 (S). The concentration of (L), (M) were 103 cfu/mL, (E) was 103 and 106 cfu/mL and (S) were 106 cfu/mL, respectively (FIG. 9A); and CL signal of cotton swab testing in the mixture of Escherichia coli Castellani and Chalmers (103 cfu/mL) and MRSA-PP7 (104 cfu/mL) by mimicking the cleaning table in healthcare facilities (FIG. 9B).
Figure 9B:
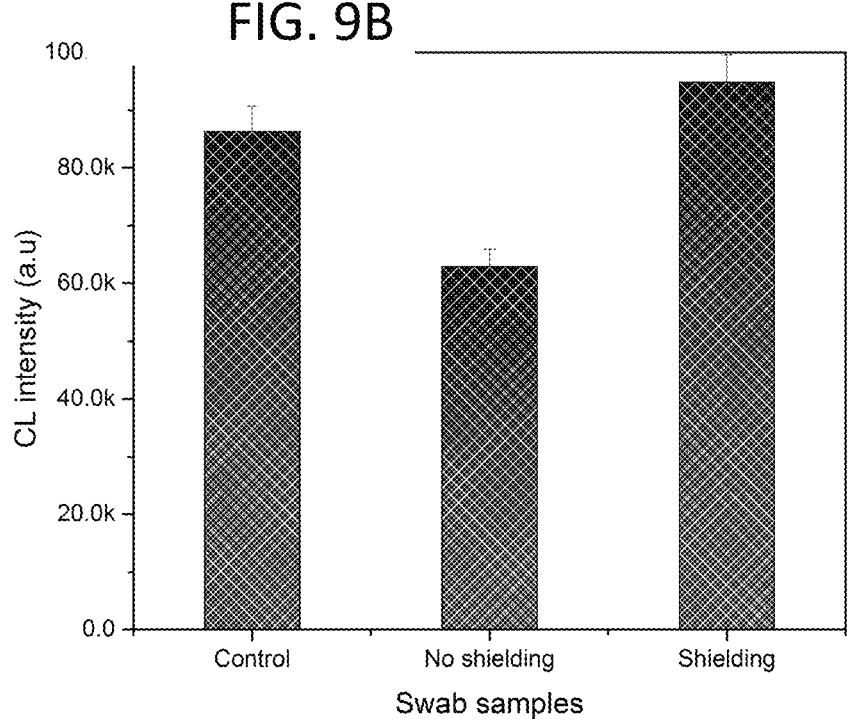
Figure 10:
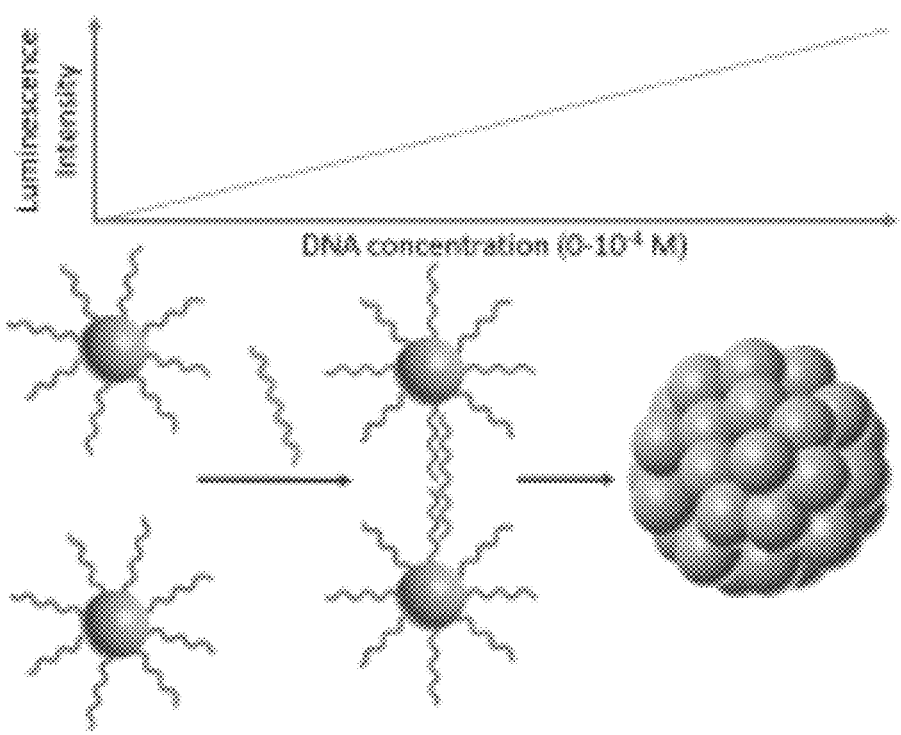
FIG. 10 illustrates the concept of nucleic acid detection using nanoaggregation-enhanced chemiluminescence. The target is added to gold nanoparticles conjugated with two different ssDNA strands complementary to the target sequence: DNA probe 1 and DNA probe 2 (grey). In the presence of the target sequence (red), gold nanoparticles aggregate into nanoballs leading to a significant increase in the chemiluminescence signal of luminol-hydrogen peroxide system (not shown here).

To evaluate the efficiency and specificity macromolecular shielding, we performed sequential screening and specific identification of MRSA bacteria in a complex sample of different classes of microorganisms with equal concentrations, including gram-negative bacteria E. coli Castellani and Chalmers, gram-positive bacteria Lactobacillus delbrueckii subsp. Bulgaricus, and the fungus Mucor circinelloides, and MRSA-SP19. The microbial mixture was treated with TCEP for 5 min before the addition of Au nanoplates and luminol and analysis with a portable luminometer. As depicted in FIG. 9A, the presence of the microorganisms in the sample results in a significant decrease in CL intensity due to the decrease in Au nanoplate oxidation as explained earlier, showing the ability to rapidly screen the sample for microbial presence. For specific identification of MRSA, a similar sample of the microbial mixture was first treated with MRSA-specific antibodies then anti-IgG-PEG before addition of TCEP, Au nanoplate and luminol (FIG. 9A). The specific detection of MRSA is reflected by an increase in CL intensity as compared to samples where MRSA was replaced with the same concentration of E. coli, or samples that contained MRSA but lacked MRSA-specific antibodies. Tests on real environmental samples using cotton swab were performed by spiking solid surfaces with a mixture of E. coli Castellani and Chalmers and MRSA-PP7 strain showed the same performance, demonstrating practical applications in sanitary testing in food processing and healthcare facilities (FIG. 9B).

Conclusions

Shown herein is application of the redox effect of TCEP and its use in a microbial detection concept. In addition to acting as a reducing agent of disulfide bonds, TCEP acts as an oxidant on thin gold nanoplates. The oxidation reaction of nanoplates continuously generates reactive radicals that induce luminescence enhancement in the presence of luminol. The results show that the generated luminescence is stable for more than 10 min but still provides luminescence intensity even after 1 hour. The reaction of TCEP with Au nanoplates and luminol was investigated and a mechanism of interaction was explained. In the presence of microorganisms, TCEP reduces the disulfide bond of the Dsbc proteins on the microbial outer layers and is concomitantly converted into its oxidized and chemically inactive form TCEP-O. This means that the presence of microorganisms prevents TCEP from oxidizing the Au nanopaltaes, thus reducing the catalytic effect on chemiluminescence proportionally to the microbial concentration. Using the dual redox activity of TCEP, a chemiluminescence assay that enables both microbial screening and identification has been disclosed. The detection of the presence of microorganisms and quantification of the microbial load was performed within 10 minutes with a limit of detection as low as 100 cfu·mL$^{-1}$ and a linear range of $10^2$-$10^7$ cfu·mL$^{-1}$. To enable specific detection with the same approach, microbial macromolecular shielding can be utilized to allow specific detection by target exclusion. Specific shielding of the microbial target with antibody-conjugated PEG polymer prevents the interaction of TCEP with the Dsbc proteins on the microbial surface, thus increasing the availability of TCEP for Au nanoplate oxidation, leading to an increase in luminescence intensity. The concept was successfully used to detect MRSA pathogens in less than 1 hour in a mixture of different microorganisms. The test was performed on environmental samples obtained using cotton swab on contaminated surfaces.

The chemiluminescence intensity can be defined as $l=k_2[.L][O_2]\emptyset$ where $k_2$ is the rate of the oxidation reaction of .L with $O_2$, and $\phi$ is the quantum efficiency of $AP^{2-}$.

Example 3

Use of Disclosed Methods for PCR-Free DNA Detection by Nanoaggregation-Enhanced Chemiluminescence Reagents Gold(III) chloride trihydrate, trisodium citrate dehydrate, sodium phosphate saline buffer (PBS), Tris (2-carboxyethyl) phosphine hydrochloride (TCEP), sodium chloride (NaCl), and luminol were purchased from Sigma-Aldrich (USA). Ethylenediaminetetraacetic acid (EDTA) was procured from Boston Bioproducts, USA. Hydrogen peroxide ($H_2O_2$) was obtained from Fluka Analytical, USA. Nanopure water (resistance of ~18.2 MΩ, filtered through a 0.2 μm filter) from a SpectraPure Lab Grade Type 1 DI system (Spectra-Pure Inc., USA) was utilized for preparation of the desired aqueous solutions (molecular biology grade). All chemicals from commercial sources were of analytical grade or the highest purity available. All the solutions and glassware were autoclaved prior to being used. Ceratocystis fagacearum (C. fagacearum) and DNA extracted from other fungal strains were collected from the United States Forest Service Northern Research Station, NRS-16, Saint Paul, USA.

Probe DNA for the specific label-free detection of C. fagacearum were identified from the internal transcribed spacer (ITS) gene region of *C. fagacearum*. All oligonucleotide sequences were procured from Integrated DNA Technologies (IDT), USA. The corresponding sequences used in the studies were as follows:

```
Probe DNA 1:
5'-ACTCAGCAATGA-thio-3' (SEQ ID NO: 1)

Probe DNA 2:
5'-thio-TGGTTAAATGCA-3' (SEQ ID NO: 2)

Target DNA sequence:
5'-TCATTGCTGAGTTGCATTTAACCA-3' (SEQ ID NO: 3)

Non-target DNA sequence:
5'-AGATTGCGATCTCCTGTCCA-3'(SEQ ID NO: 4).
```

Synthesis of Gold Nanoparticles (AuNPs).

All glassware used for AuNPs synthesis was cleaned in Nochromix solution followed by Aqua Regia (3 parts HCl and 1 part HNO3) according to a standard laboratory procedure. The synthesis of citrate-stabilized AuNPs was based on a modification of Turkevich's method (Grabar, K. C., Freeman, R. G., Hommer, M. B. & Natan, M. J. Preparation and characterization of Au colloid monolayers. Anal. Chem. 67, 735-743 (1995)). Briefly, a 100 mL solution of 1 mM HAuCl4 was boiled under stirring and uniform temperature until the formation of bubbles was observed. The solution was then heated for another 25 min. Then, 10 mL of preheated trisodium citrate (38.8 mM) was quickly added to the boiling HAuCl4 solution. During this process, the solution turns colorless for a moment followed by a transition from violet to dark-ruby/red. The solution was heated for another 5 min before cooling down to room temperature. The final reddish solution of AuNPs was stored at room temperature and covered with aluminum foil. The size of AuNPs was characterized to be 10±2 nm in diameter using transmission electron microscopy (TEM, FEI Technai T12).

Preparation of Fungal Cultures.

All of the fungal isolates of *C. fagacearum* and the other oak-associated fungi (*Ophiostoma quercus, Didymella glomerata, Alternaria alternata, Diplodia corticola, Penicillium* brevicompactum, Pezicula pseudocinnamomea, and unknown Pleosporales sp.) were grown on potato dextrose agar (PDA) (Difco) in 100 mm dia Petri plates for 7 to 14 days at 24° C.

*C. fagacearum* Detection Via Isolation.

Standard phytopathological protocols were used to isolate the pathogen from sapwood of branch and/or stem samples from diseased red oaks (Pokorny, J. How to collect field samples and identify the oak wilt fungus in the laboratory. NA-FR-01-99. USDA Forest Service, Northeastern Area State and Private Forestry, St. Paul, Minn. (1999)). Bark tissue was sprayed with 95% EtOH, flame-sterilized and then carefully peeled to reveal outer sapwood areas with vascular discoloration characteristic of *C. fagacearum* colonization. Small pieces of discolored tissue were excised using a sterilized wood gouge and then plated on PDA amended with 20% lactic acid (4 ml/1000 ml media). Plates were incubated on the laboratory bench in clear plastic boxes at ambient temperature (~24° C.) and standard room lighting for up to 14 days. Resulting fungal growth was either examined directly when pure cultures were obtained or sub-culturing performed to obtain pure isolates. The fungus was identified on the basis of colony appearance and presence of endoconidia.

Fungal DNA Extraction for Use in PCR and Chemiluminescence Assays.

Fungal DNA was extracted from pure isolates of the fungi (*C. fagacearum*, as well as the other fungi used for specificity testing) growing on PDA and for *C. fagacearum* from drill shavings obtained from exposed, discolored vascular tissue of branch or stem samples taken from diseased red oaks (Yang, A. & Juzwik, J. Use of nested and real-time PCR for the detection of Ceratocystis fagacearum in the sapwood of diseased oak species in Minnesota. Plant Disease 101, 480-486 (2016)). For fungal colonies, DNA for the internal transcribed spacer (ITS) region was extracted per manufacturer's instructions for a commercial kit (DNeasy Plant Mini Kit, Qiagen). For drill shavings, DNA for the same region was extracted per manufacturer's instructions for a different kit (QIAamp DNA Stool Kit, Qiagen). Each extraction yielded 200 μl of extracted DNA for use in nested PCR and chemiluminescence assays for detection of *C. fagacearum.*

*C. fagacearum* Detection Via PCR Technique.

A recently published nested PCR protocol was used to amplify the pathogen DNA resulting from culture and from wood extractions (Id). The first round of amplification was performed with general ITS primers (ITS1F and ITS4) and the second round with specific primers CF01 and CF02 developed by Wu et al. (Wu, C. P. et al. Rapid and accurate detection of Ceratocystis fagacearum from stained wood and soil by nested and real-time PCR. Forest Pathol. 41, 15-21 (2011)). Amplification protocol was per manufacturer's instructions (QIAamp Mini Stool Kit, Qiagen) as used by Yang and Juzwik. Lysis buffer without template DNA was used for negative controls while extracted DNA from previously identified fungal cultures of *C. fagacearum* were used for positive controls for drill shaving samples. Visualization of the PCR product using 2% agarose gel resulted in an amplicon size of 280 bp when *C. fagacerarum* was present. Verification was done by sequencing the PCR products and comparing resulting DNA sequences to those in GenBank.

*C. fagacearum* Detection Via Chemiluminescence Technique.

DNA specific to *C. fagacearum* was detected by chemiluminescence technique using two AuNPs-probe DNA conjugates. CL reaction was conducted using luminol (0.2 mg mL-1) and $H_2O_2$ (10 mM). The CL spectra were recorded with GloMax-Multi Jr Single-Tube Multimode Reader (Promega Biosystems Sunnyvale, Inc., USA). Aggregation of AuNPs was also confirmed by microscopic imaging techniques, i.e. field emission gun—scanning electron microscopy (FEG-SEM-JEOL 6500) and transmission electron microscopy (TEM, FEI Technai T12).

Results and Discussion

Figure 12A:
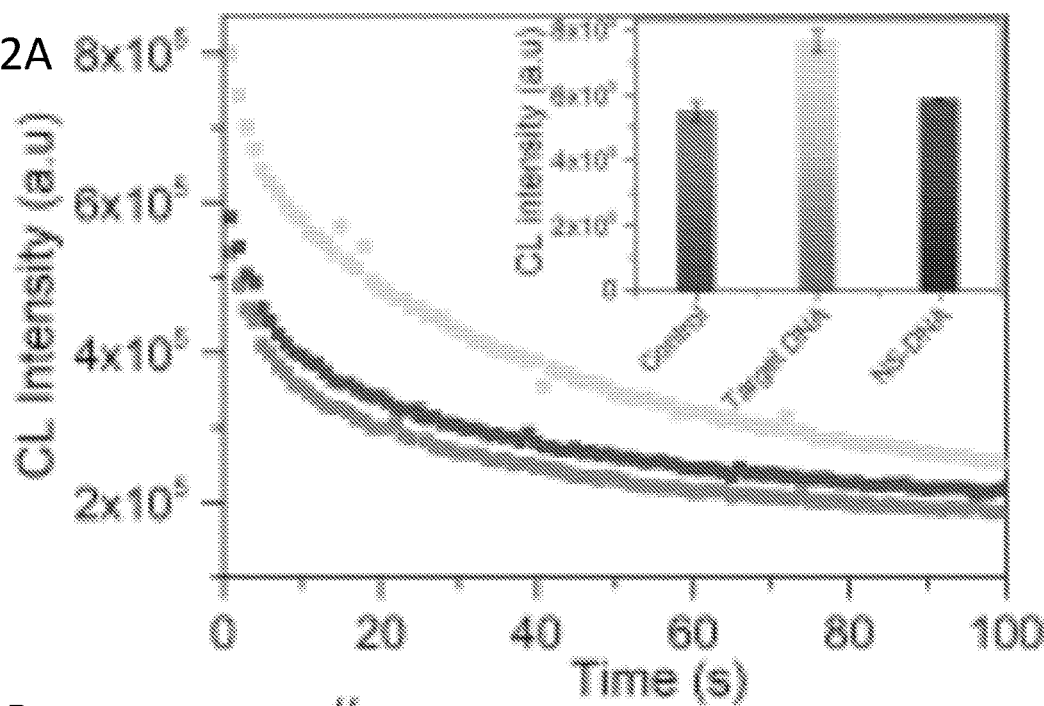
FIGS. 12A and 12B illustrate the chemiluminescence detection of C. fagacearum DNA. Variation of chemiluminescence intensity over time for the control sample (red), for the AuNPs-DNA probes after a target DNA (green) and a non-target (NS) DNA (blue) were added. The inset represents the chemiluminescence signal intensity obtained for the above mentioned samples during the first seconds of measurements (FIG. 12A). Linear regression dependence of the chemiluminescence intensity as a function of the target DNA concentration (y=23507.6x+565141.3, r2=0.98) (FIG. 12B).
Figure 12B:
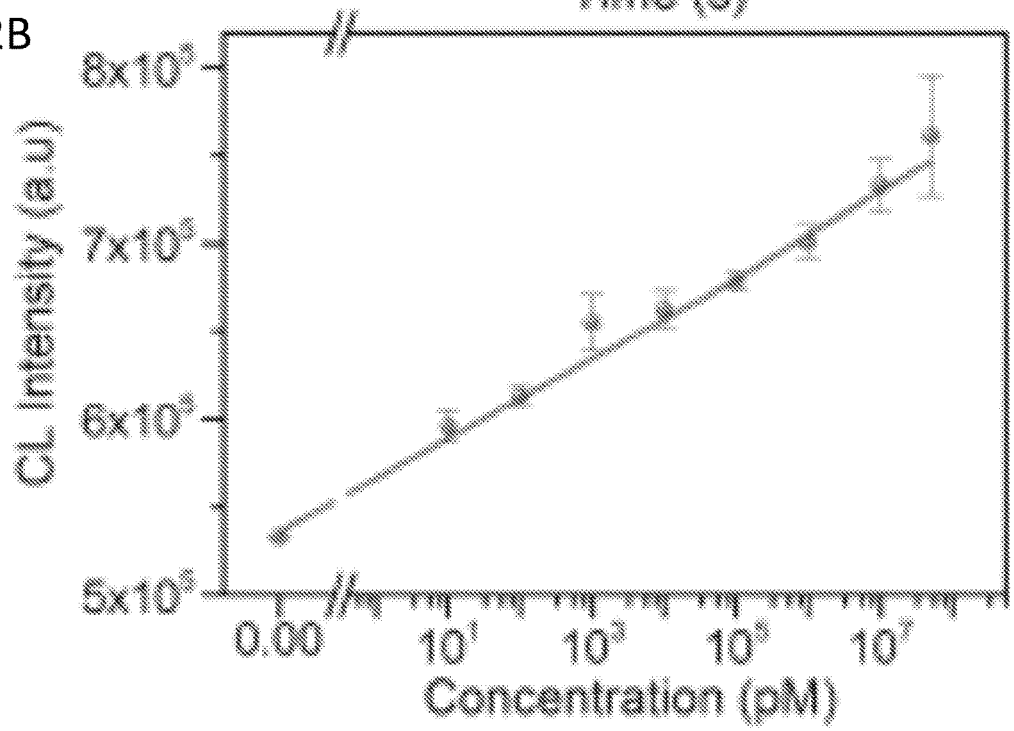
Figure 13A:
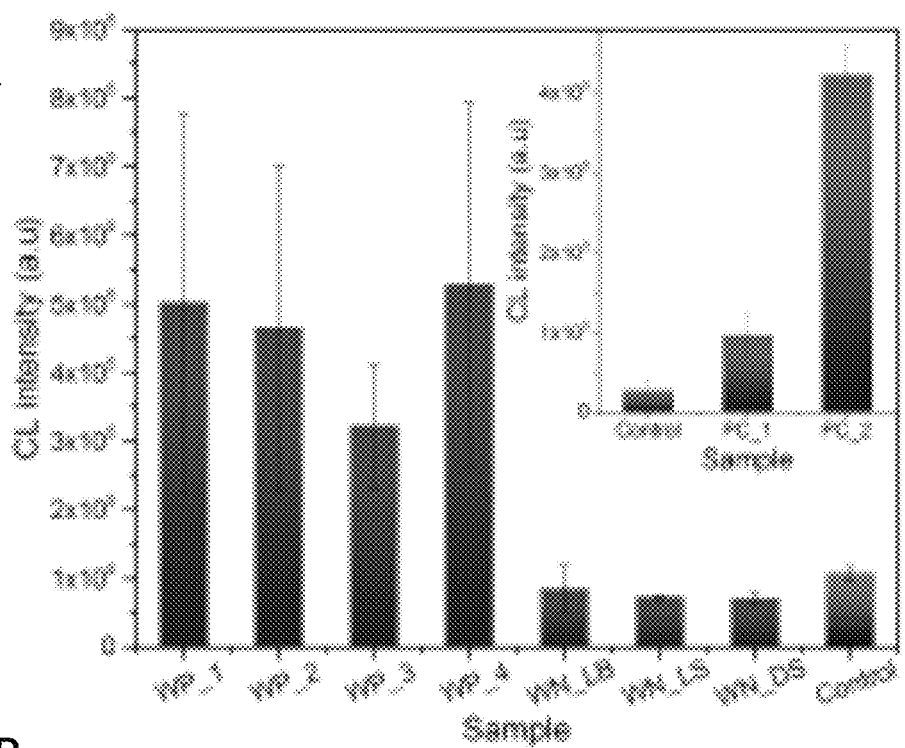
FIGS. 13A, 13B and 13C illustrates the specificity and selectivity of C. fagacearum detection with AuNPs-DNA probes. A specificity study using wood positive WP (first four columns), and wood negative WN samples (dead stem DS, live branch LB, and live stem LS) and a control (AuNPs-DNA probes with no DNA introduced). Inset shows the CL signals of DNA samples from C. fagacearum pure culture PC (FIG. 13A) Gel electrophoresis of amplified fungal DNA: 1—negative control (water), 2 —C. fagacearum negative wood sample, 3 to 5 —C. fagacearum positive wood sample, 6 and 7—pure C. fagacearum culture), L—DNA ladder. The red arrow indicates the size of a target DNA band (FIG. 13B). Selectivity studies using differentt oak-associated fungi: Ophiostoma quercus (OQ), Didymella glomerate (DG), Alternaria alternate (AA), Diplodia corticola (DC), Penicillium brevicompactum (PB), Unknown Pleosporales sp (UPS), and Pezicula pseudocinnamomea (PP) (FIG. 13C).
Figure 13B:
Figure 13C:
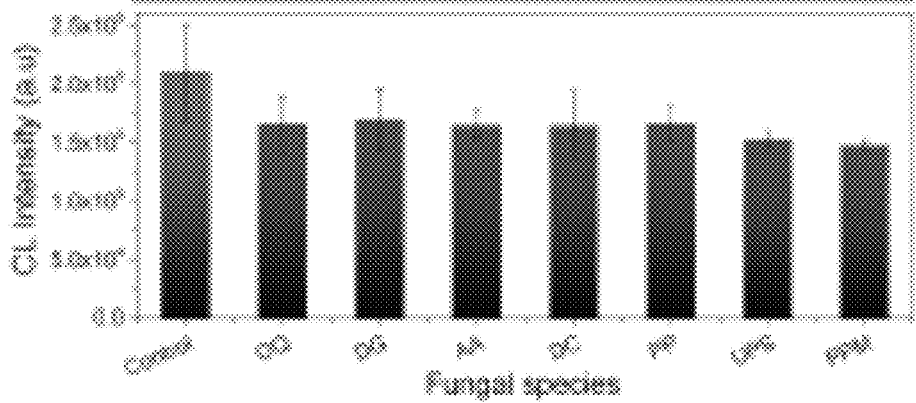

To demonstrate the concept of nanoparticle aggregation-enhanced chemiluminescence, the fungus Ceratocystis fagacearum was used as a model pathogen. *C. fagacearum* is the causal agent of oak wilt, a destructive disease of oak trees that causes significant ecological impact, depletion of natural resources, and a growing economic impact.

Rapid and accurate detection *C. fagacearum* is essential for disease survey efforts and for implementation of control actions. Because specific antibodies are not available for this pathogen, detection is currently performed by visual diagnostics, fungal isolation and microscopic identification, or nucleic acid detection. Following artificial inoculation, *C. fagacearum* is moves undetected through the transpiration stream of a red oak tree for 2 to 3 weeks without expression of leaf symptoms. Crown wilt is then exhibited, and an infected tree may die within 4-6 weeks of inoculation. Vascular system colonization in species of the white oak group (e.g., *Q. macrocarpa, Q. alba*) occurs more slowly and the patterns of crown wilt development are different than those in red oaks and may be confused with other diseases. Oak wilt diagnosis in white oak group species is particularly problematic and generally requires laboratory confirmation. While PCR-based detection can be costly (e.g. $120 per sample for one diagnostic laboratory) and requires use of labor-intensive protocols by laboratory-trained personnel, isolation of the pathogen on agar media is time consuming (7-14 days for of the plate growth) and largely ineffective in the dormant season of the pathogen. Hence, there is a significant need for a rapid and more cost-effective technique for early diagnosis of oak wilt.

Incorporation of metal nanoparticles such as Au, Ag, Pt, Zn/Cu into a chemiluminescence reaction has been largely shown to enhance the chemiluminescence signal through a combination of different mechanisms that are largely affected by the nanoparticle size (Zhang, Z. F., Cui, H., Lai, C. Z. & Liu, L. J. Gold nanoparticle-catalyzed luminol chemiluminescence and its analytical applications. Anal. Chem. 77, 3324-3329 (2005) and Zhang, S., Zhong, H. & Ding, C. Ultrasensitive flow injection chemiluminescence detection of DNA hybridization using signal DNA probe modified with Au and CuS nanoparticles. Anal. Chem. 80, 7206-7212 (2008)). Since heterogeneous catalysis is a surface or interface phenomenon, the nanogold catalytic effect increases with the available active surface area of the nanoparticle, which increases with decreasing nanoparticle size (Zhang, Z. F., Cui, H., Lai, C. Z. & Liu, L. J. Gold nanoparticle-catalyzed luminol chemiluminescence and its analytical applications. Anal. Chem. 77, 3324-3329 (2005)). However, the catalytic effect is also affected by the electron density or plasmonic field around the nanoparticles, which reaches its maximum intensity for nanoparticle's size around 30-50 nm, and decreases for sizes outside that range (Zhang, Z. F., Cui, H., Lai, C. Z. & Liu, L. J. Gold nanoparticle-catalyzed luminol chemiluminescence and its analytical applications. Anal. Chem. 77, 3324-3329 (2005)). As a result, the profile of the catalytic effect of AuNPs on chemiluminescence seems to match the profile of the localized surface plasmon resonance intensity as a function of the nanoparticle size.

In this example, the AuNPs-probe DNA conjugates were prepared using the nucleotide sequences with size of 4.08 nm each. The probe DNA 1 and probe DNA 2 had the length of 12 bases each and given the dimension of a single nucleotide (3.4 Å), the length of each probe DNA was 40.8 Å or 4.08 nm (without impact of terminal SH-groups as linkers for DNA-AuNPs coupling).

Detection of the target was based on hybridization event between two complementary DNA probes (coupled to AuNPs) with the target DNA strand. Binding of the target to the DNA probes leads to the formation of the nanoparticle dimers, in which the strands of DNA probes get attracted to each for the distance of around 8-10 nm. Such distance causes coupled plasmon resonance of AuNPs (plasmon coupling occurs since AuNPs approach each other to the distance shorter than a diameter of one nanoparticle, i.e. 10±2 nm). The intensity of electric fields near the particles' surface decreases with the increase of the inter-particle distance, with an optimum intensity obtained at distances below 10 nm. Assembling nanoparticles gives rise to hot spots in the electromagnetic field distribution.

Therefore, the maximum sensitivity of detection in the AuNPs-based systems can be achieved when the target molecule is placed in the inter-particle gap (Abbas, A., Fei, M., Tian, L. & Singamaneni, S. Trapping proteins within gold nanoparticle assemblies: dynamically tunable hot-spots for nanobiosensing. Plasmonics 8, 537-544 (2013)). This gap is the most sensitive region generated by the plasmon coupling of assembled nanoparticle dimers or agglomerates.

At the same time, we did not use shorter nucleotide strands that would decrease distance between AuNPs. Nucleotides should have the proper lengths to provide the specific detection of the target: hybridization of two DNA probes with target strand should eliminate possible interferences with non-targets.

Based on these characteristics, we hypothesized that the assembly or aggregation of gold nanoparticles would also affect the catalytic activity of the plasmonic nanoparticles and thus would induce a change in chemiluminescence intensity. Consequently, detection methods based on nanoparticle aggregation could be easily monitored using chemiluminescence while providing higher sensitivity then colorimetry or UV-visible absorption spectroscopy. FIG. 10 shows an illustration of the concept employed in this work for detection of the target DNA where chemiluminescence enhancement originates from the nanoparticle aggregation.

To test this hypothesis, the chemiluminescence of the system luminol-hydrogen peroxide ($H_2O_2$) in the presence of 10±2 nm AuNPs-DNA probes before and after their aggregation caused by DNA hybridization were compared. To prepare the detection probes (AuNPs-DNA probe 1 and AuNPs-DNA probe 2), AuNPs were conjugated with two thiolated ssDNA sequences each of them was complementary to different parts of a target sequence located within the genomic DNA of *C. fagacearum*. When the target sequence is added to the reaction medium, the DNA probes recognize and hybridize with the target, leading to the aggregation of the nanoparticles into thin layers or spherical agglomerates depending on the target concentration. The aggregation of AuNPs is confirmed by absorption spectroscopy, transmission electron microscopy (TEM) and scanning electron microscopy (See FIGS. 11A-11F). The aggregation results in a significant increase in the chemiluminescence signal intensity as depicted in FIG. 12A. The increase in luminescence is proportional to the increase in the target DNA concentration (FIG. 12B), indicating a linear correlation (y=23507.6x+565141.3, r2=0.98), with a limit detection down to 260 fM, calculated according to published methods (Armbruster, D. A. & Pry, T. Limit of blank, limit of detection and limit of quantitation. Clin. Biochem. Rev. 29, S49-S52 (2008)).

The correlation between the CL intensity and concentration of the target DNA (has been explained by relation of DNA concentration in the sample to the degree of nanoparticle aggregation. The assembly of AuNPs has a significant effect on the optical properties of nanoparticles that reflects in excitation of localized surface plasmons of particles. LSPR is, thus, a very suitable and handy tool for real-time monitoring of the assembly process. Plasmon coupling that happen during formation of the nanoparticles agglomerates was also shown by Abbas et al (Abbas, A., Kattumenu, R., Tian, L. & Singamaneni, S. Molecular linker-mediated self-assembly of gold nanoparticles: understanding and controlling the dynamics. Langmuir 29, 56-64 (2012)). There are mainly two driven forces for the aggregation of AuNPs to happen: one is the target-guided assembling that brings AuNPs close to each other (cross-linking); and another is salt-induced deterioration of the electrostatic repulsion forces between citrate-stabilized AuNPs (non-cross-linking). With the use of LSPR spectroscopy, it has been demonstrated that addition of the linker reagent (p-aminothiophenol or cysteine) to the AuNPs solution makes a second plasmonic band in the UV-visible extinction spectra to appear at higher wavelengths that was due to the plasmonic coupling of assembled nanoparticles. It was shown that together with shifting over higher wavelengths, the second band also increased in intensity. That spectral change was associated with the progressive aggregation of the nanoparticles into chains and branched network and demonstrated by the authors in SEM and surface enhanced Raman scattering studies. It has also been shown that the aggregation of AuNPs was an important effect factor for the catalytic activity of AuNPs on luminol CL system. The catalytic effect of aggregated AuNPs was explained by the possible decrease in their surface negative charge density compared to AuNPs in the dispersed state (Qi, Y. & Li, B. Enhanced effect of aggregated gold nanoparticles on luminol chemiluminescence system and its analytical application. Spectrochim. Acta A 111, 1-6 (2013)).

When replacing the target DNA sequence with a random (nonspecific) sequence, no aggregation and no change in luminescence intensity is observed, indicating the specific detection of the DNA sequence from *C. fagacearum*. The detection was performed in less than 22 min using a portable luminometer (time not including sample preparation, i.e., DNA extraction from the sample matrix).

To confirm the specificity of the proposed homogenous assay, the *C. fagacearum*-positive and *C. fagacearum*-negative samples were analyzed. These include DNA extracted from the pure *C. fagacearum* culture (PC), DNA extracted from the wood shavings obtained from the oak trees infected with *C. fagacearum* (wood positive; WP), and DNA extracted from the wood shavings obtained from the healthy oak trees (wood negative; WN).

First, the DNA sample from pure culture was tested and showed a clear enhancement in the luminescence as compared to the control sample (Inset in FIG. 13A). The control sample was represented by AuNPs-DNA probe 1 and AuNPs-DNA 2 in one system in the absence of any detecting compound. Afterwards, the analysis was performed on the DNA extracts from real-world samples. FIG. 13A shows that the *C. fagacearum*-positive samples showed remarkably high chemiluminescence signal while the *C. fagacearum*-negative samples (obtained from the dead stem (DS), live stem (LS), live branch (LB) of oak trees) showed a weak signal, comparable to that of the control sample.

The samples analyzed by chemiluminescence detection were also subjected to the analysis by nested polymerase chain reaction (PCR) technique to confirm the presence or absence of the target DNA associated with *C. fagacearum*. As depicted in the electrophoresis gel in FIG. 13B, the control sample (Lane 1) and the negative wood samples (WN, lane 2) showed no band, confirming the absence of *C. fagacearum* colonization. Lane 3-5 containing positive samples (WP) reveal a single band of 280 bp, confirming *C. fagacearum* infection. Lanes 6 and 7 shows the same band obtained from DNA extracted from pure *C. fagacearum* culture (PC). The band in lane 7 is slightly smeared due to the high concentration of DNA extracted from the pure culture. Thus, PCR detection results were consistent with the results obtained with the chemiluminescence assay.

To evaluate the specificity and the absence of cross-reactivity in the newly developed diagnostic method for *C. fagacearum*, we have tested 8 other oak-associated fungi, including *Ophiostoma quercus* (OQ), Didymella *glomerata* (DG), *Alternaria alternata* (AA), *Diplodia* corticola (DC), *Penicillium* brevicompactum (PB), unknown Pleosporales sp. (UPS), and Pezicula pseudocinnamomea (PP). First, these fungi were identified by isolation and purification of cultures, extraction of DNA, PCR using ITS1F/ITS4 primer pairs, and PCR products sequenced. Following identification, additional extracted DNA was used in detection experiments using chemiluminescence.

FIG. 13C shows that all analyzed samples exhibited a weak signal intensity comparable to the control sample confirming the specificity of the proposed method to *C. fagacearum* uniquely and the absence of cross-reactivity with other oak-associated fungi.

CONCLUSIONS

In conclusion, we report a novel DNA detection method using the enhancement effect of plasmonic nanoparticle aggregation on chemiluminescence. Nanoparticle aggregation is caused by the hybridization of the target DNA with DNA probes attached to gold nanoparticles. The method was demonstrated by the specific detection of *C. fagacearum*, the causal agent of wilt in oak trees, and confirmed by isolation on agar and by PCR. The developed method enabled DNA detection at an extremely low level (260 fM). Beside the low cost of the reagents required and the simplicity of the detection procedure, this new method eliminates the need for enzymes and extensive conjugation methods. Furthermore, upon extraction of DNA from the sample matrix, the detection of DNA can be determined within 22 min using a portable luminometer. Once further simplification of DNA extraction steps from real-world samples is achieved, this technique would easily be translated into a rapid, in-field test kit with a hand-held reader.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

The complete disclosure of all patents, patent applications, and publications, and electronically available material cited herein are incorporated by reference in their entirety.

All headings are for the convenience of the reader and should not be used to limit the meaning of the text that follows the heading, unless so specified.

Thus, embodiments of methods for microbial screening and identification are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial
<220> FEATURE:
<223> OTHER INFORMATION: Probe

<400> SEQUENCE: 1
actcagcaat ga                                                          12

<210> SEQ ID NO 2
<211> LENGTH: 12
<212> TYPE: DNA
<213> ORGANISM: Artificial
<220> FEATURE:
<223> OTHER INFORMATION: Probe

<400> SEQUENCE: 2
tggttaaatg ca                                                          12

<210> SEQ ID NO 3
<211> LENGTH: 24
<212> TYPE: DNA
<213> ORGANISM: Ceratocystis fagacearum

<400> SEQUENCE: 3
tcattgctga gttgcattta acca                                             24

<210> SEQ ID NO 4
<211> LENGTH: 20
<212> TYPE: DNA
<213> ORGANISM: Ceratocystis fagacearum

<400> SEQUENCE: 4
agattgcgat ctcctgtcca                                                  20
```

Also herein, the recitations of numerical ranges by endpoints include all numbers subsumed within that range (e.g., 1 to 5 includes 1, 1.5, 2, 2.75, 3, 3.80, 4, 5, etc.). The recitation of numbers include any ranges that can be formed from such numbers (e.g., recitation of 1, 10, 15 and 100 includes ranges of 1 to 10, 1 to 15, 1 to 100, 10 to 15, 10 to 100 and 15 to 100).

For any method disclosed herein that includes discrete steps, the steps may be conducted in any feasible order, unless context indicates otherwise. And, as appropriate, any combination of two or more steps may be conducted simultaneously.

The invention claimed is:

1. A method of detecting the presence of microorganisms in a sample, the method comprising:

combining a sample, a reducing agent, an oxidant generator and a chemiluminescent agent, wherein the reducing agent both reduces the oxidant generator to produce an oxidant and reduces one or more disulfide bonds a surface of a microorganism and wherein the oxidant oxidizes the chemiluminescent agent to produce a luminescent compound; and detecting the presence or absence of a signal from the luminescent compound to indicate the presence or absence of microorganisms in the sample, wherein the intensity of the signal is inversely proportional to the amount of microorganisms in the sample.

2. The method according to claim 1 further comprising combining the sample with a shielding agent before combining it with the reducing agent.

3. The method according to claim 2 further comprising subjecting another sample to the combining and detecting steps and comparing the signals between the two samples to determine an amount of a specific type or class of microorganism.

4. The method according to claim 1, wherein the reducing agent comprises a compound containing one or more hydroxyl or carboxyl groups.

5. The method according to claim 1, wherein the reducing agent comprises tris(2-carboxyethyl)phosphine (TCEP).

6. The method according to claim 1, wherein the chemiluminescent agent comprises luminol.

7. The method according to claim 1, wherein the oxidant generator comprises gold, copper, zinc, or combinations thereof.

8. The method according to claim 1, wherein the oxidant generator comprises gold nanoparticles.

9. The method according to claim 1, wherein the oxidant generator comprises gold nanoplates or gold nanotriangles.

10. The method according to claim 9, wherein the oxidant generator comprises gold nanoplates or gold nanotriangles having an average size of 200+25 nm and thicknesses less than 5 nm.

11. The method according to claim 1, wherein the shielding agent comprises a receptor and a macromolecular polymer.

12. The method according to claim 11, wherein the receptor comprises antibodies, enzymes, aptamers, or molecular receptors.

13. The method according to claim 11, wherein the macromolecular polymer comprises chitosan, polyethylene glycol (PEG), or combinations thereof.

14. The method according to claim 11, wherein the macromolecular polymer comprises organic polymer, organometallic polymer, or combinations thereof that have an overall charge (zeta potential) opposite to the surface charge or zeta potential of the target microorganism.

* * * * *

UNITED STATES PATENT AND TRADEMARK OFFICE
CERTIFICATE OF CORRECTION

PATENT NO. : 10,767,234 B2
APPLICATION NO. : 15/943000
DATED : September 8, 2020
INVENTOR(S) : Abdennour Abbas and Minh-Phuong Ngoc Bui Page 1 of 1

It is certified that error appears in the above-identified patent and that said Letters Patent is hereby corrected as shown below:

In the Claims

In Column 28, Line 65, delete "bonds a surface" and replace with --bonds on a surface--

Signed and Sealed this
Twentieth Day of July, 2021

Drew Hirshfeld
*Performing the Functions and Duties of the
Under Secretary of Commerce for Intellectual Property and
Director of the United States Patent and Trademark Office*